(12) United States Patent
Allen et al.

(10) Patent No.: US 8,557,809 B2
(45) Date of Patent: Oct. 15, 2013

(54) TRIAZOLOPYRIDINE COMPOUNDS AS PIM KINASE INHIBITORS

(75) Inventors: Shelley Allen, Boulder, CO (US); Robert Kirk DeLisle, Boulder, CO (US); Julie Marie Greschuk, Boulder, CO (US); Erik James Hicken, Boulder, CO (US); Joseph P. Lyssikatos, Piedmont, CA (US); Fredrik P. Marmsater, Boulder, CO (US); Mark C. Munson, Boulder, CO (US); John E. Robinson, Boulder, CO (US); Qian Zhao, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 265 days.

(21) Appl. No.: 13/059,881

(22) PCT Filed: Aug. 18, 2009

(86) PCT No.: PCT/US2009/054198
§ 371 (c)(1),
(2), (4) Date: Feb. 18, 2011

(87) PCT Pub. No.: WO2010/022081
PCT Pub. Date: Feb. 25, 2010

(65) Prior Publication Data
US 2011/0144100 A1 Jun. 16, 2011

Related U.S. Application Data

(60) Provisional application No. 61/089,958, filed on Aug. 19, 2008.

(51) Int. Cl.
| | | |
|---|---|---|
| *A61K 31/5377* | (2006.01) | |
| *A61K 31/496* | (2006.01) | |
| *A61K 31/4709* | (2006.01) | |
| *C07D 471/04* | (2006.01) | |
| *A61P 35/02* | (2006.01) | |
| *A61P 29/00* | (2006.01) | |

(52) U.S. Cl.
USPC ............... 514/233.2; 514/303; 514/253.06; 546/119; 544/128; 544/363

(58) Field of Classification Search
USPC .......... 514/233.2, 253.06, 303; 544/363, 128; 546/119
See application file for complete search history.

(56) References Cited

U.S. PATENT DOCUMENTS

| | | |
|---|---|---|
| 2005/0256309 A1 | 11/2005 | Altenbach et al. |
| 2007/0154919 A1 | 7/2007 | Korn et al. |
| 2007/0173508 A1 | 7/2007 | Hutchinson et al. |
| 2008/0027063 A1 | 1/2008 | Zhao et al. |
| 2008/0261988 A1 | 10/2008 | Bearss et al. |
| 2009/0042918 A1 | 2/2009 | Kearney et al. |

FOREIGN PATENT DOCUMENTS

| | | |
|---|---|---|
| EP | 1277754 A1 | 1/2003 |
| WO | 01/34603 A2 | 5/2001 |
| WO | 02/012236 A1 | 9/2002 |
| WO | 02/072579 A1 | 9/2002 |
| WO | 2004/058749 A1 | 7/2004 |
| WO | 2004/058769 A2 | 7/2004 |
| WO | 2005/028624 A2 | 3/2005 |
| WO | 2006/018727 A2 | 2/2006 |
| WO | 2006/058752 A1 | 6/2006 |
| WO | 2007/044724 A2 | 4/2007 |
| WO | 2008/082839 A2 | 7/2008 |
| WO | 2008/121687 A2 | 10/2008 |

OTHER PUBLICATIONS

Wilson et al., Journal of Organic Chemistry (1959), 24, 1046-51.*
International Search Report corresponding to PCT Application No. PCT/US2009/054198, (2009).
Chemcats Accession No. 205019468, Chembridge Screening Library, (2009).
Bullock, Alex N. et al., "Structural Basis of Inhibitor Specificity of the Human Protooncogene Proviral Insertion Site in Moloney Murine Leukemia Virus (PIM-1) Kinase", J. Med. Chem, 2005, 48, 7604-7614.
Pierce, Albert C., et al., "Docking Study Yields Four Novel Inhibitors of the Protooncogene Pim-1 Kinase", J. Med. Chem, 2008, 51, 1972-1975.

* cited by examiner

*Primary Examiner* — Niloofar Rahmani

(74) *Attorney, Agent, or Firm* — John R. Moore, Esq.; Sarah S. Mastous; Viksnins Harris & Padys PLLP

(57) ABSTRACT

Compounds of Formula (I): I in which B, $R^1$, $R^{1a}$, $R^2$, $R^3$, $R^4$, $R^5$, $R^6$, $R^7$, $R^{10}$ and $R^{11}$ have the meanings given in the specification, are receptor tyrosine inhibitors useful in the treatment of diseases mediated by PIM-1 and/or PIM-2 and/or PIM-3 kinases.

17 Claims, No Drawings

TRIAZOLOPYRIDINE COMPOUNDS AS PIM KINASE INHIBITORS

The present invention relates to novel compounds, to pharmaceutical compositions comprising the compounds, to a process for making the compounds and to the use of the compounds in therapy. More particularly, it relates to certain triazolopyridine compounds useful in the treatment and prevention of diseases which can be treated with a PIM kinase inhibitor, including diseases mediated by PIM kinases. Particular compounds of this invention have been found to be inhibitors of PIM-1 and/or PIM-2 and/or PIM-3.

Protein kinases constitute a family of structurally related enzymes that are responsible for the control of a vast array of cellular processes.

The PIM kinase sub-family consists of three distinct serine/threonine protein kinase isoforms (PIM-1, -2 and -3) belonging to the calmodulin-dependent protein kinase-related (CAMK) group. PIM-2 and PIM-3 are respectively 58% and 69% identical to PIM-1 at the amino acid level.

The over-expression of PIM-1 has been reported in various human lymphomas and acute leukemias (Amson, R. et al, *Proc. Natl. Acad. Sci. U.S.A.,* 1989, 86: 8857-8861). PIM-1 has been shown to synergize with c-Myc to drive lymphomagenesis (Breuer M., et. al., *Nature,* 1989, 340; 61-63), and plays an important role in cytokine signaling in T-cell development (Schmidt, T., et. al., *EMBO J,* 1998, 17:5349-5359). In addition, there is evidence that PIM-1 is over-expressed in prostatic neoplasia and human prostate cancer (Valdman, A. et al, *The Prostate,* 2004, 60: 367-371; Cibull, T. L. et al, *J. Clin. Pathol.,* 2006, 59: 285-288) and may serve as a useful biomarker in identification of prostate cancer (Dhanasekaran, S. M. et al, *Nature,* 2001, 412(13): 822-826). PIM-1 has been shown to be critical for IL-6 mediated proliferation of hematopoietic cells (Hirano, T., et. al. *Oncogene* 2000, 19:2548-2556), as well as STAT3 mediated cell cycle progression (Shirogane, T., et al., *Immunity* 1999, 11:709.

Recently, it has been discovered that PIM-1 is up-regulated by Flt-3 and may play an important role in Flt-3 mediated cell survival (Kim, K. T. et al *Neoplasia,* 2005, 105(4): 1759-1767). Since Flt-3 itself is implicated in leukemias like AML, additional knockdown of PIM-1 may be a useful approach to treating leukemias driven by Flt-3 or various mutations. Accordingly, PIM-1 inhibitors may be useful as therapeutic agents for a variety of cancers such as hematological cancers.

PIM-2 is a highly conserved serine/threonine kinase involved in cell proliferation and the prevention of apoptosis (Baytel et al., Biochim. Biophys. Acta Gene Struct. Expr. 1442: 274 (1998)). PIM-2 is upregulated in AML, CLL, and possibly in prostate cancer.

PIM-3 is a proto-oncogene identified in pancreatic liver and colon cancers, and is an apoptotic regulator (Popivanova, B., et al., Cancer Sci., 98(3): 321 (2007)).

Based upon the direct involvement of the PIM kinases in a wide variety of cancers downstream of STAT3/5 activation, it is expected that inhibition of the PIM kinases will result in inhibition of proliferation and survival of multiple cancer cell types. This would then be expected to provide a therapeutic benefit to cancer patients with a variety of cancers (both solid tumor and hematologic settings), as well as other conditions that are mediated by PIM kinase signaling.

In addition to the malignant cells detailed above, PIM kinases are also expressed in hematopoietically-derived cell lines and hematopoietically-derived primary cells including cells of the immune system such as B cells, T cells, monocytes, macrophages, eosinophils, basophils, and dendritic cells. Expression of PIM kinases can be induced, for example, by cytokines which utilize Jak/Stat signaling, such as IL-2, IL-3, IL-4, IL-5, IL-6, IL-7, IL-9, IL-12, IL-15, GM-CSF, IFNα, IFNγ, erythropoietin, thrombopoietin, and prolactin, and the generation, differentiation, maintenance and activation of hematopoietically-derived cells is dependent on these cytokines Moreover, PIM proteins have been shown to be required for the efficient proliferation of peripheral T cells mediated by T-cell receptor and IL-2 signaling (Mikkers, et al., Mol. Cell. Biol., 2004, 6104). Although the exact mechanism of action of PIM kinases in an immunological setting has yet to be fully defined, they have been reported to phosphorylate a number of substrates involved in cellular proliferation, differentiation, and survival (Bullock et al., J. Biol. Chem., 2005 280:41675; Chen et al., PNAS 2002 99:2175; Dautry et al. J. Biol. Chem. 1998 263:17615).

Chronic and acute inflammatory and autoimmune diseases are associated with the overproduction of pro-inflammatory cytokines and activation of immune cells against the body's own tissues. However, many of these diseases are not adequately treated by current therapies and/or these therapies have significant side effects/risks.

A particular example of an autoimmune disease is multiple sclerosis (MS). MS is a progressive central nervous system (CNS) inflammatory autoimmune disease wherein the immune system mounts responses against CNS components. The resulting damage to axons and nerves leads to progressive neurological impairment and significant disability. MS affects over 2.5 million people worldwide (www.nationalmssociety.org); however many current therapies are only moderately effective and have questionable risk factors A need therefore remains for compounds and methods for treating autoimmune and inflammatory diseases.

International patent application, publication number WO 2004/058769 discloses, inter alia, certain 3-aryl and 3-N-arylamino-substituted [1,2,4]triazolo[4,3-b]pyridazines purported to inhibit several protein kinases, including PIM-1.

It has now been found that certain [1,2,4]triazole[4,3-a] pyridine compounds bearing a quinolinyl group at the 3 position of the triazolopyridine ring are inhibitors of PIM kinases, in particular PIM-1 and/or PIM-2 and/or PIM-3 kinases, which are useful for treating diseases such as cancers and inflammatory diseases. In addition, compounds of the invention may be useful for treating immune cell-associated diseases and disorders, such as inflammatory and autoimmune diseases.

Accordingly, provided is a compound of the general Formula I:

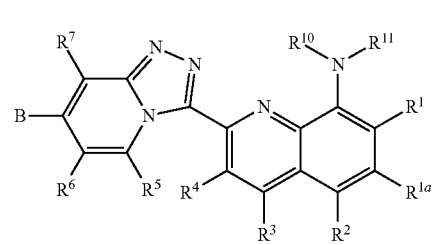

or a pharmaceutically acceptable salt thereof, wherein:
$R^{10}$ and $R^{11}$ together with the N to which they are attached form a 4-8 membered heterocyclic ring optionally having an additional ring heteroatom selected from N and O, wherein the heterocyclic ring is optionally substituted with one or more $R^9$ groups;

each $R^9$ is independently selected from halogen, (1-6C) alkyl, $NR^fR^g$, -(1-6C alkyl)$NR^hR^i$, $OR^j$, (1-6C alkyl)$OR^k$, $C(O)NR^mR^n$, $C(O)O$(1-6C alkyl), and -(1-6C alkyl)$NR^hC(O)O$(1-6C alkyl);

B is H, $OR^a$, (1-6C alkyl)$NR^bR^c$, (1-6C alkyl)OH, $NR^bR^c$, or $CH(OH)CH_2OH$;

$R^1$ is H, F, Cl, Br, methyl, ethyl, cyclopropyl or CN;

$R^{1a}$, $R^2$, $R^3$ and $R^4$ are independently H, F, Cl, Br, methyl, ethyl, cyclopropyl or CN;

$R^5$ and $R^7$ are independently H, F, Me or CN;

$R^6$ is H, F, Me, Br, CN, ethyl, cyclopropyl or phenyl;

$R^a$ is H, (1-6C alkyl), -(1-6C alkyl)-O-(1-6C alkyl) or -(1-6C alkyl)-O-(3-6C cyclo alkyl);

each $R^b$, $R^c$, $R^d$, $R^e$, $R^f$, $R^g$, $R^h$, $R^i$, $R^j$, $R^k$, and $R^m$ is independently selected from H and (1-6C alkyl); and $R^n$ is H, (1-6C alkyl) or O-(1-6C alkyl).

The term "$C_1$-$C_6$ alkyl" as used herein refers to saturated linear or branched-chain monovalent hydrocarbon radicals of one to six carbon atoms, respectively. Examples include, but are not limited to, methyl, ethyl, 1-propyl, 2-propyl, 1-butyl, 2-methyl-1-propyl, 2-butyl, 2-methyl-2-propyl, 2,2-dimethylpropyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

In certain embodiments, $R^1$ is H.

In certain embodiments, $R^{1a}$ is selected from H, F and Cl.

In certain embodiments, $R^{1a}$ is H. In certain embodiments, $R^{1a}$ is F. In certain embodiments, $R^{1a}$ is Cl.

In certain embodiments, $R^2$ is selected from H and F.

In certain embodiments, $R^2$ is H. In other embodiments, $R^2$ is F.

In certain embodiments, $R^3$ is H.

In certain embodiments, $R^4$ is H.

In certain embodiments, $R^5$ is H.

In certain embodiments, $R^6$ is H.

In certain embodiments, $R^7$ is H.

In certain embodiments, each of $R^5$, $R^6$ and $R^7$ is H.

In certain embodiments, each of $R^1$, $R^{1a}$, $R^2$, $R^3$, $R^4$, $R^5$, $R^6$ and $R^7$ is H.

The phrase "$R^{10}$ and $R^{11}$ together with the N to which they are attached form a 4-8 membered heterocyclic ring" refers to a group having the formula —$NR^{10}R^{11}$ representing a 4-8 membered saturated heterocyclic radical having at least one ring nitrogen atom. The heterocyclic ring optionally has an additional ring heteroatom selected from N and O, the remaining ring atoms being carbon.

In certain embodiments, the —$NR^{10}R^{11}$ group forms a 5-7 membered heterocyclic ring. In certain embodiments, the heterocyclic ring is substituted with one or more $R^9$ groups, for example 1-4 $R^9$ groups, and as a further example 1-2 $R^9$ groups.

Particular examples of heterocyclic rings represented by —$NR^{10}R^{11}$ include piperidinyl, piperazinyl, and morpholinyl ring systems. In certain embodiments, the heterocyclic ring is substituted by 1-4 $R^9$ groups, for example 1-2 $R^9$ groups.

In certain embodiments, $R^9$ is $CF_3$.

In certain embodiments, $R^9$ is (1-6C)alkyl. Examples include methyl, ethyl, and propyl. A particular example is Me.

In certain embodiments, $R^9$ is $NR^fR^g$. Examples include groups where $R^f$ is H or Me and $R^g$ is H, methyl, ethyl, propyl, isopropyl, butyl, or isobutyl. Particular values of $R^9$ when represented by $NR^fR^g$ include $NH_2$.

In certain embodiments, $R^9$ is (1-6C alkyl)$NR^hR^i$. Examples include groups where $R^h$ is H and $R^i$ is H or alkyl.

Particular values of $R^9$ when represented by -(1-6C alkyl)$NR^hR^i$ include $CH_2NR^hR^i$, for example $CH_2NH_2$.

In certain embodiments, $R^9$ is $OR^j$. Examples include groups where is H or (1-6C) alkyl, for example methyl. A particular example is OH.

In certain embodiments, $R^9$ is (1-6C alkyl)$OR^k$. Examples include groups where $R^k$ is H. A particular example is $CH_2OH$.

In certain embodiments, $R^9$ is $C(O)NR^mR^n$. Examples include groups where $R^m$ and $R^n$ are independently H or (1-6C) alkyl, for example methyl. A particular example is $C(O)NH_2$.

In certain embodiments, $R^9$ is C(O)O(1-6C alkyl). Examples include $CO_2Me$ and $CO_2Et$.

In certain embodiments, $R^9$ is (1-6C alkyl)$NR^hC(O)O$(1-6C alkyl). Examples include groups where $R^h$ is H. Particular values include $CH_2NR^hC(O)O$(1-6C alkyl), for example $CH_2NHCO_2t$-Bu.

In certain embodiments, the heterocyclic ring represented by —$NR^{10}R^{11}$ is a 5-7 membered heterocyclic ring which is unsubstituted or substituted with one or more $R^9$ groups independently selected from Me, $NH_2$, $CH_2NH_2$, OH, $CH_2OH$, C(O)OMe, $C(O)NH_2$ and $CH_2NHCO_2t$-Bu. In certain embodiments, the heterocyclic ring represented by $NR^{10}R^{11}$ is substituted with one or two of said $R^9$ groups.

Particular embodiments of heterocyclic rings represented by —$NR^{10}R^{11}$ include the structures:

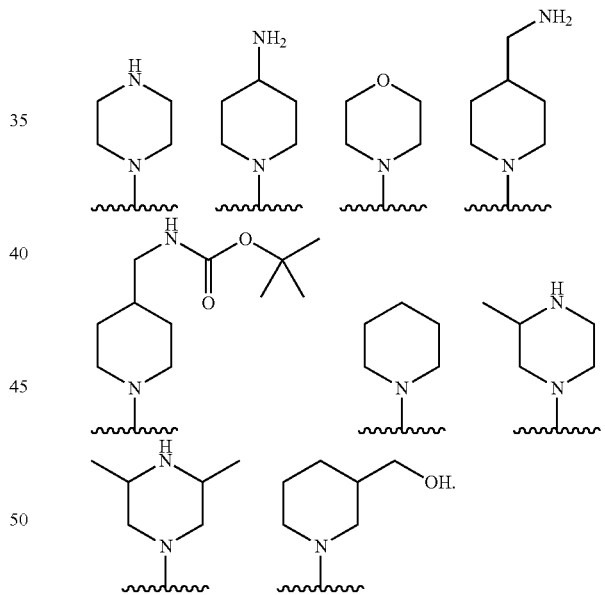

In certain embodiments, B is H.

In certain embodiments, B is $OR^a$.

Examples of B when represented by $OR^a$ include groups wherein $R^a$ is (1-6C)alkyl. Particular values include OMe, OEt and O-(isobutyl). Particular mention is made of OMe.

Examples of B when represented by $OR^a$ include groups wherein $R^a$ is -(1-6C alkyl)-O-(1-6C alkyl). Particular values of $OR^a$ include —$OCH_2CH_2OMe$ and —$OCH_2CH_2CH_2OMe$. Particular mention is made of —$OCH_2CH_2OMe$.

Examples of B when represented by $OR^a$ include groups wherein $R^a$ is -(1-6C alkyl)-O-(3-6C cycloalkyl). A particular of $OR^a$ includes —$OCH_2CH_2O$(cyclopropyl).

In certain embodiments, B is (1-6C alkyl)NR$^b$R$^c$. In certain embodiments, R$^b$ is H. In certain embodiments, R$^c$ is H. In other embodiments, R$^c$ is (1-6C)alkyl. Examples include groups having the formula CH$_2$NR$^b$R$^c$, for example CH$_2$NHEt and CH$_2$NH$_2$.

In certain embodiments, B is (1-6C alkyl)OH. A particular value of B is CH$_2$OH.

In certain embodiments, B is CH(OH)CH$_2$OH.

It will be appreciated that certain compounds according to the invention may contain one or more centers of asymmetry and may therefore be prepared and isolated in a mixture of isomers such as a racemic mixture, or in an enantiomerically pure form.

It will further be appreciated that the compounds of Formula I or their salts may be isolated in the form of solvates, and accordingly that any such solvate is included within the scope of the present invention.

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I.

According to another aspect, the present invention provides a process for the preparation of a compound of Formula I or a salt thereof as defined herein which comprises:

(a) coupling a corresponding compound having the formula II

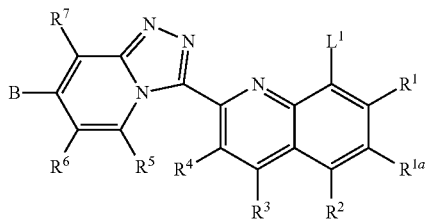

II wherein L$^1$ represents a leaving atom or group, with a compound having the formula HNR$^{10}$R$^{11}$ wherein NR$^{10}$R$^{11}$ represents a 4-8 membered heterocyclic ring optionally having an additional heteroatom selected from N and O and optionally substituted with one or more R$^9$ groups, using a palladium catalyst and a ligand in the presence of a base; or (b) reacting a compound of Formula III

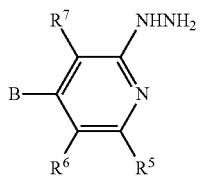

III with a compound having the Formula IV

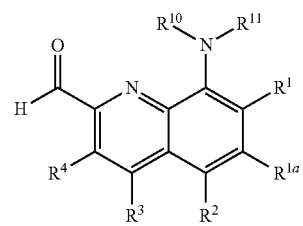

IV in the presence of an organo hypervalent iodine reagent; or (c) for a compound of Formula I where B is —OR$^a$, reacting a corresponding compound having the Formula V

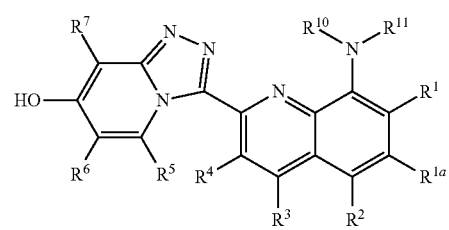

V with a compound of the formula R$^a$-L$^2$, wherein L$^2$ represents a leaving atom or group, in the presence of a base;

(d) for a compound of Formula I wherein B is —(CH$_2$)NR$^b$R$^c$, reacting a corresponding compound having the Formula VI

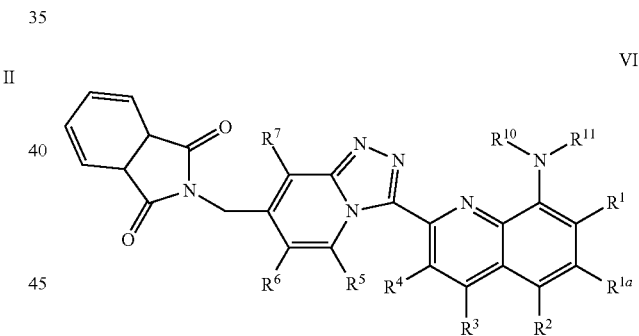

VI with hydrazine; and removing any protecting group or groups and, if desired, forming a salt.

Referring to method (a), the leaving atom L$^1$ may be, for example, a halide such as Br or I. Alternatively, L$^1$ may be a leaving group, such as a hydrocarbylsulfonyloxy group, for example, a triflate group, or an arylsulfonyloxy group or an alkylsulfonyloxy group, such as a tosylate or a mesylate group. Suitable palladium catalysts include Pd$_2$(dba)$_3$ and Pd(OAc)$_2$. Suitable ligands include rac-BINAP or DIPHOS. The base may be, for example, an alkali metal carbonate or alkoxide, such as for example cesium carbonate or sodium tert-butoxide. Convenient solvents include aprotic solvents such as ethers (for example tetrahydrofuran or p-dioxane) or toluene. The coupling of a compound of formula (II) with HNR$^{10}$R$^{11}$ can be conveniently performed at a temperature between 0° C. and reflux, and more particularly at reflux.

Referring to method (b), the organo hypervalent iodine reagent refers to any hypervalent iodine reagent suitable for forming heterocyclic rings. Examples include iodobenzene diacetate (IBD) and [hydroxy(tosyloxy)iodo]benzene (HTIB), which can be prepared by treating IBD with p-toluenesulfonic acid monohydrate in acetonitrile. Suitable solvent systems when using IBD include methanolic potassium hydroxide. Suitable solvent systems when using HTIB include neutral solvents, for example acetonitrile or dioxane. The reaction can be performed at a temperature ranging from 0 to 60° C.

Referring to method (c), the leaving atom $L^2$ may be, for example a halogen atom such as Br, Cl or I. Alternatively, $L^2$ can be a leaving group, for example an arylsulfonyloxy group or an alkylsulfonyloxy group, such as a mesylate or a tosylate group. The base may be, for example, an alkali metal hydride or carbonate, such as sodium hydride, potassium hydride, sodium carbonate, potassium carbonate or cesium carbonate. Convenient solvents include aprotic solvents such as ethers (for example tetrahydrofuran or p-dioxane), DMF, or acetone. The reaction can be conveniently performed at a temperature ranging from −78 to 100° C.

Referring to method (d), the reaction is conveniently performed at ambient temperature. Suitable solvents include alcohols such as methanol.

A compound of Formula II

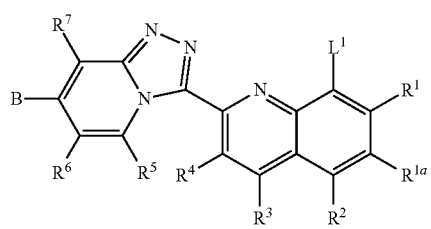

II can be prepared by cyclizing a corresponding compound having the formula VII

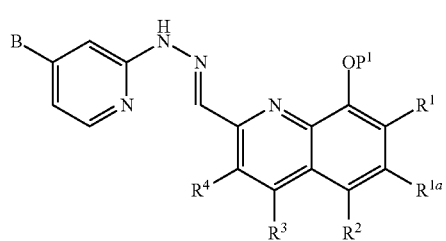

VII where $P^1$ is an alcohol protecting group, in the presence of an organo hypervalent iodine reagent as described above, followed by deprotection of the alcohol group and conversion of the alcohol group to an alkylsulfonyloxy group, such as a triflate group.

The compounds of the formulas II and VII are believed to be novel and are provided as further aspects of the invention.

The ability of test compounds to act as PIM-1, PIM-2 or PIM-3 inhibitors may be demonstrated by the assay described in Examples A, B and C, respectively.

Compounds of Formula I have been found to be inhibitors of PIM-1 and/or PIM-2 and/or PIM-3, and are useful for treating diseases and disorders which can be treated with a PIM-1 and/or PIM-2 and/or PIM-3 kinase inhibitor, including diseases mediated by PIM-1 and/or PIM-2 and/or PIM-3 kinases. Particular compounds of this invention are inhibitors of PIM-1 and therefore are useful in treating diseases and disorders mediated by PIM-1, such as cancers, such as hematological cancers and solid tumors (e.g., breast cancer, colon cancer, gliomas).

Examples of hematological cancers include, for instance, leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma (MM). Additional examples of hematological cancers include myeloproliferative disorders (MPD) such as polycythemia vera (PV), essential thrombocytopenia (ET) and idiopathic primary myelofibrosis (IMF/IPF/PMF). Certain cancers which can be treated with compounds of Formula I are cancers which of hematological origin, such as, but not limited to, cancers derived from T cells or B cells.

In addition, certain compounds according to the present invention may be useful for the treatment of inflammatory disorders mediated by T and B cells function, such as rheumatoid arthritis, lupus, multiple sclerosis, and inflammatory bowel disease.

Accordingly, a further embodiment of this invention provides a method of treating cancer in a mammal in need thereof, comprising administering to said mammal a compound of Formula I or a pharmaceutically acceptable salt thereof. In one embodiment, the cancer is of hematological origin. In one embodiment, the cancer derives from T cells. In one embodiment, the cancer derives from B cells.

A further embodiment of this invention provides a compound of Formula I or a pharmaceutically acceptable salt thereof, for use in the treatment of cancer. In one embodiment, the cancer is of hematological origin. In one embodiment, the cancer derives from T cells. In one embodiment, the cancer derives from B cells.

Another embodiment of this invention provides a method of treating or preventing inflammatory and autoimmune diseases, comprising administering to a mammal in need thereof an effective amount of a compound of Formula I. Examples of diseases which can be treated include inflammatory or autoimmune diseases. In one embodiment, the disease is multiple sclerosis. In another embodiment, the disease is lupus. In another embodiment, the disease is inflammatory bowel disease.

A further embodiment of this invention provides a compound of Formula I for use in treating an inflammatory or autoimmune disease. In one embodiment, the disease is multiple sclerosis. In another embodiment, the disease is lupus. In another embodiment, the disease is inflammatory bowel disease.

Expression of PIM kinases in immune cells can be induced by cytokines present during immune responses. Immune cells are critically dependent on cytokines for differentiation and development of effector functions during normal and pathogenic immune responses. Thus, compounds of the invention may be useful for treating diseases and disorders characterized by aberrant cytokine production and responses and/or aberrant immune cell activation.

Accordingly, another embodiment of the invention provides a method of treating diseases and disorders characterized by aberrant cytokine production and responses and/or aberrant immune cell activation in a mammal in need thereof, comprising administering to the mammal a compound of Formula I or a pharmaceutically acceptable salt thereof.

Examples of disease and disorders which can be treated using a compound of Formula I include transplant rejection and autoimmune and inflammatory diseases and disorders. Examples of autoimmune diseases and disorders include multiple sclerosis (MS), systemic lupus erythematosis, inflammatory bowel disease (IBD), Crohn's disease, irritable bowel syndrome, pancreatitis, ulcerative colitis, diverticulosis, Grave's disease, arthritis (including rheumatoid arthritis, juvenile rheumatoid arthritis, osteoarthritis, psoriatic arthritis and ankylosing spondylitis), myasthenia gravis, vasculitis, autoimmune thyroiditis, dermatitis (including atopic dermatitis and eczematous dermatitis), psoriasis, scleroderma, asthma, allergy, systemic sclerosis, vitiligo, graft vs. host disease (GVHD), Sjogren's syndrome, glomerulonephritis, IgA nephoropathy, diabetes mellitus (type I) and asthma.

Particular examples of diseases and disorders which can be treated using a compound of Formula I include autoimmune and inflammatory diseases. Particular examples of such diseases include asthma, MS, inflammatory bowel disease (IBD), lupus, psoriasis and rheumatoid arthritis.

Another embodiment provides a compound of Formula I or a pharmaceutically acceptable salt thereof for use in the treatment of diseases and disorders characterized by aberrant cytokine production and responses and/or aberrant immune cell activation in a mammal. Examples of such diseases and disorders include autoimmune and inflammatory diseases.

A subset of the triazolopyridine compounds disclosed herein was found to have an $IC_{50}$ for PIM-1 that is at least 10 fold less than the $IC_{50}$ for PIM-2. As a further example, particular triazolopyridine compounds disclosed herein were found to have an $IC_{50}$ for PIM—that is at least 100 fold less than the $IC_{50}$ for PIM-2. Accordingly, also provided are triazolopyridine compounds which are highly potent PIM-1 inhibitors and are highly selective for PIM-1 relative to PIM-2.

A subset of the triazolopyridine compounds disclosed herein were found to have an $IC_{50}$ for PIM-1 that is at least 10 fold less than the $IC_{50}$ for PIM-2 and an $IC_{50}$ for PIM-3 approximately equivalent to that observed for PIM-1. As a further example, particular triazolopyridine compounds disclosed herein were found to have an $IC_{50}$ for PIM-1 that is at least 100 fold less than the $IC_{50}$ for PIM-2, and $IC_{50}$ for PIM-3 approximately equivalent to that observed for PIM-1. Accordingly, also provided are triazolopyridine compounds which are highly potent PIM-1/PIM-3 dual inhibitors and are highly selective for PIM-1 and PIM-3 relative to PIM-2.

As used herein, the term treatment includes prophylaxis as well as treatment of an existing condition.

Accordingly, another aspect of this invention provides a method of treating diseases or medical conditions in a mammal mediated by a PIM-1 and/or PIM-2 and/or PIM-3 kinase, comprising administering to said mammal one or more compounds of Formula I or a pharmaceutically acceptable salt or prodrug thereof in an amount effective to treat or prevent said disorder.

Compounds of Formula I may also be useful as adjuvants to cancer treatment, that is, they can be used in combination with one or more additional drugs, for example a chemotherapeutic that works by the same or by a different mechanism of action.

Compounds of the present invention may also be used in combination with one or more additional drugs, for example an anti-inflammatory compound, an immunosuppressive compound or an immunodepleting agent that works by the same or a different mechanism of action.

The phrase "effective amount" means an amount of compound that, when administered to a mammal in need of such treatment, is sufficient to (i) treat or prevent a particular disease, condition, or disorder mediated by a PIM-1 and/or PIM-2 and/or PIM-3 kinase, (ii) attenuate, ameliorate, or eliminate one or more symptoms of the particular disease, condition, or disorder, or (iii) prevent or delay the onset of one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

Compounds of the invention may be administered by any convenient route, e.g. into the gastrointestinal tract (e.g. rectally or orally), the nose, lungs, musculature or vasculature, or transdermally or dermally. Compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

According to another aspect, the present invention provides a pharmaceutical composition, which comprises a compound of Formula I or a pharmaceutically acceptable salt thereof, as defined hereinabove. In one embodiment, the pharmaceutical composition includes the compound of Formula I together with a pharmaceutically acceptable diluent or carrier.

According to another aspect, the present invention provides a compound of Formula I or a pharmaceutically acceptable salt thereof, for use in therapy, such as the treatment of a PIM-1 and/or PIM-2 and/or PIM-3 kinase-mediated condition.

According to a further aspect, the present invention provides the use of a compound of Formula I, or a pharmaceutically acceptable salt thereof, for use in the treatment of a PIM-1 and/or PIM-2 and/or PIM-3 kinase-mediated condition, as defined hereinabove.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), dichloromethane (DCM, methylene chloride), toluene, and dioxane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters).

Example A

Enzyme PIM-1 Assay

The assay for the determination of PIM-1 activity is based on the incorporation of [$^{33}$P]PO$_4$ from [$\gamma$-$^{33}$P]ATP into PIM2tide substrate and capture of the radiolabeled peptide onto a Whatman P81 (phosphocellulose) filter plate. The amount of radiolabeled product is then measured by liquid scintillation counting. The final buffer conditions were as follows: 20 mM K$^+$MOPS, pH 7.4, 10 mM MgCl$_2$, 0.005% Tween-20, 1 mM DTT. Assay mixtures contained 35 μM [$\gamma$-$^{33}$P]ATP (20 pfi/mL), 7.5 μM PIM2tide and 0.25 nM PIM-1 in a total volume of 50 μL. Incubations were carried out for 60 min at 22° C. and quenched with 75 μL of 200 mM H$_3$PO$_4$, filtered through a Whatman P81 plate and washed (1×200 μL and 5×100 μL) with 200 mM H$_3$PO$_4$. Fifty μL of liquid scintillation cocktail were then added per well, and the plate was counted for 30 s/well using a TopCount NXT.

IC$_{50}$ Determinations:

Compounds were prepared at 50× the final concentration in DMSO by conducting 3-fold serial dilutions from a 500-μM intermediate dilution to give a 10-point dosing curve having a high dose of 10 μM. One-μL aliquots of these were then transferred to the assay mixtures above to give a final concentration of DMSO of 2%. A standard or reference compound was typically included on each assay plate to validate that plate. For each plate, percent of control (POC) values were calculated for each well. IC$_{50}$'s were estimated from the POC's using a standard 4-parameter logistic model. The IC$_{50}$ is defined as the concentration of inhibitor at which the POC equals 50 for the fitted curve. Compounds of Formula I were found to have an average IC$_{50}$ below 10 μM when tested in this assay. Specific IC$_{50}$ values are provided in Table 1.

Example B

PIM-2 Assay

Assay was performed as described in Example A, using 4 μM [$\gamma$-$^{33}$P]ATP (20 μCi/mL), 1.0 μM PIM2tide and 1.5 nM GST-tagged recombinant full-length human Pim-2 in place of PIM-1. Compounds of Formula I were found to have an average IC$_{50}$ below 10 μM when tested in this assay. Specific IC$_{50}$ values are provided in Table 1.

Example C

PIM-3 Assay

Assay was performed as described in Example A, using 30 μM [$\gamma$-$^{33}$P]ATP (20 μCi/mL), 3.75 μM PIM2tide and 0.5 nM recombinant rat PIM-3 in place of PIM-1. Compounds of Formula I were found to have an average IC$_{50}$ below 10 μM when tested in this assay. Specific IC$_{50}$ values are provided in Table 1.

TABLE 1

| Example No. | PIM-1 IC$_{50}$ (nM) | PIM-2 IC$_{50}$ (nM) | PIM-3 IC$_{50}$ (nM) |
| --- | --- | --- | --- |
| 1 | 255 | 10000 | 554 |
| 2 | 179 | 10000 | ND |
| 3 | 24 | 2305 | 60 |
| 4 | 2793 | 10000 | ND |
| 5 | 24 | 2598 | 121 |
| 6 | 31 | 2977 | 105 |
| 7 | 17 | 3591 | 105 |
| 8 | 54 | 10000 | 189 |
| 9 | 11 | 543 | 24 |
| 10 | 3 | 224 | 13 |
| 11 | 84 | 2600 | 217 |
| 12 | 3 | 92 | 4 |
| 13 | 2 | 29 | 4 |
| 14 | 4 | 509 | 20 |
| 15 | 15 | 2080 | ND |
| 16 | 3 | 185 | 10 |
| 17 | 77 | 1958 | 51 |
| 18 | 32 | 736 | 25 |
| 19 | 18 | 1798 | ND |
| 20 | 48 | 2379 | ND |
| 21 | 7 | 142 | ND |
| 22 | 270 | 3097 | ND |
| 23 | 22 | 647 | 62 |
| 24 | 150 | 10000 | ND |
| 25 | 128 | 3022 | ND |
| 26 | 21 | 613 | 62 |
| 27 | 34 | 570 | 38 |

ND: Not determined

Example D

Cellular Proliferation Assay

The assay for determination of the antiproliferative activity of multiple PIM inhibitors in the JAK2-driven cell lines is conducted as follows. Cells are plated out to 96-well plates at an initial density of 10,000 cells/well in 95 μL. Compounds are prepared at 20× the final concentration in DMSO by conducting 3-fold serial dilutions to give a 10-point dosing curve having a high dose of 1000 μM. Aliquots (5 μL) of these dilutions are then transferred to the appropriate wells of the 96-well plates containing cells to yield a final DMSO concentration of 0.5%. The cells are then incubated with compound for 72 hours at 37° C., 5% CO$_2$. CelltiterBlue reagent (Promega, Catalog #: G8080) is then added (20 μL/well) and incubated at 37° C., 5% CO$_2$ for 1-8 hours depending on the cell line being analyzed. The plate is then quantified employing a fluorescence plate reader (Model: Gemini [Molecular Devices]; Settings: 560 nm (Ex)/590 nm (Em) 570 nm (cut-off) [CellTiter Blue Assay].

The values for each well are then converted to a percent of untreated control (POC). These POC values are then plotted as a function of compound concentration. A 4-parameter curve-fit analysis is performed for each compound dilution and an IC$_{50}$ value is calculated from this curve.

Example E

T Cell In Vitro Functional Assays

The in vitro assays which can be used to assess the effects of the compounds of the invention are described in assays A, B, C and D below. CD4+ T cells are isolated from red blood cell-depleted splenocytes of C57Bl/6J mice (Jackson Laboratories, catalog #000664) using CD4+ T cell isolation kit (Miltenyi, catalog #130-090-860).

In assay (A), purified CD4+ T cells are plated in 96 well plates at 90000 cells/well in 90 μL. A dilution series of the compounds are prepared at 100× the final concentration in DMSO and then diluted 10-fold into complete media (10× stocks). 10 μL of 10× compound stocks are added to appropriate wells of 96 well plates containing cells and incubated for 1 hour at 37° C., 5% $CO_2$. The cell/compound mixtures are then transferred to a 96 well plate coated with anti-CD3 mAb (1 μg/mL; BD Pharmingen, catalog #553057) and soluble anti-CD28 mAb (1 μg/mL; BD Pharmingen, catalog #553294) was added. Plates are cultured at 37° C., 5% $CO_2$ for 40 hours. 20 μL of the culture are removed for determination of proliferation using the CellTitre-Glo™ luminescent assay (Promega, Catalog #G7571) according to the manufacturer's protocol. The plate is quantified on a Packard Top-Count instrument using luminescence protocol and data analyzed using Prism software.

In assay (B), purified CD4+ cells are treated with compound and stimulated as described for assay (A). After 40 hours, supernatants are assayed for IL-2 using R&D duo set ELISA kits (catalog #DY402). ELISA plates are quantified relative to a standard curve using Molecular Devices Versamax Reader at 450 nM and Softmax Pro software.

In assay (C), 1,000,000 cells/mL of purified CD4+ T cells are mixed with 1 μg/mL anti-CD28, 10 ng/mL IL-4 (R&D Systems cat #404-ML-010/CF) and 2 μg/mL anti-IFNγ (R&D Systems catalog #AB-485-NA) and placed into plates coated with 1 μg/mL anti-CD3. After 5 days, cells are harvested, washed and incubated overnight at 37° C., 5% $CO_2$. The following day, 50,000 cells are plated into each well of a 96 well plate. A dilution series of compounds are prepared at 200× the final concentration in DMSO, then 10× stocks are prepared by dilution in cell culture media. 10 μL of 10× stocks are added to the cells in the 96-well plate and incubated for 2 hours at 37° C., 5% $CO_2$. Cell/compound mixtures are then transferred to well coated with 0.1 μg anti-CD3 and incubated at 37° C., 5% $CO_2$. Culture supernatants are removed 18 hours later and tested for IL-4 levels by ELISA (R&D Systems catalog #DY404). ELISA plates are quantified relative to a standard curve using Molecular Devices Versamax Reader at 450 nM and Softmax Pro software.

In assay (D), 1,000,000 cells/mL of purified CD4+ T cells are mixed with 1 μg/mL anti-CD28, 50 ng/mL IL-6 (R&D Systems cat #406-ML-025/CF), 1 ng/mL TGFβ (R&D Systems cat #303-B2-002), 2 μg/mL anti-IL-4 (R&D Systems catalog #AB-404-NA), 2 μg/mL anti-IFNγ (R&D Systems catalog #AB-485-NA) and placed into plates coated with 1 μg/mL anti-CD3. After 4 days, cells are harvested, washed and 100,000 cells are plated into 96 well plate. A dilution series of compounds are prepared at 200× the final concentration in DMSO, then 10× stocks are prepared by dilution in cell culture media. 10 μL of 10× stocks are added to the cells in the 96 well plate. After 2 hours, 50 ng IL-23 (R&D Systems catalog #1887-ML-010/CF) is added to each well and 18 hours later supernatants are removed and tested for IL-22 levels by ELISA (R&D Systems catalog #M2200). ELISA plates are quantified relative to a standard curve using Molecular Devices Versamax Reader at 450 nM and Softmax Pro software.

Example F

T Cell In Vivo Functional Assay

The effect of compounds of Formula I on T cell responses can be determined by the following experiment. On Day 0, C57BL/6 (Jackson Laboratories #000664, 6-8 weeks of age) are immunized at the base of the tail with 100 μg of hen egg lysozyme (HEL; Sigma #L7773) with complete Freund's adjuvant (CFA; Sigma #F5881). Starting on Day 0 and continuing until Day 7, mice are dosed twice a day by oral administration with vehicle (water) or the compound of Formula I (200 mg/kg). On Day 7, popiteal lymph nodes are removed, single cell suspensions are prepared and 500,000 cells in 200 μL are activated in 96 well plates with the indicated dose of HEL peptide. Following incubation for 72 hours at 37° C., 5% $CO_2$, supernatants are harvested for IFNγ ELISA (R&D Systems catalog #MIF00) and proliferation is assessed using the CellTitre-Glo™ luminescent assay (Promega, Catalog #G7571) with both assays performed according to the manufacturer's protocol. ELISA plates are quantified relative to a standard curve using Molecular Devices Versamax Reader at 450 nM and Softmax Pro software; proliferation was quantitated on a Packard TopCount instrument using luminescence protocol and data analyzed using excel software.

Example G

B Cell In Vivo Functional Assay

The effect of a compound of Formula I on B cell responses can be determined with the following experiment. On Day 0, C57BL/6J mice (Jackson Laboratories #000664, 6-8 weeks of age) are immunized at the base of the tail with 20 μg of hen egg lysozyme (HEL; Sigma #L7773) with complete Freund's adjuvant (CFA; Sigma #F5881). Mice are re-immunized on day 7 with 20 μg HEL in alum (Pierce catalog #77161). Starting on Day 0 and continuing through Day 28, mice are dosed once a day by oral administration with vehicle (water) or the compound of Formula I (200 mg/kg). Serum is collected on days 0, 7, 14, 21, and 28 and analyzed for HEL-specific total IgG, IgG1, IgG2a, IgG2b, and IgG3 antibody production by capture ELISA (antibodies purchased from Invitrogen, catalog Nos. M30007, M32107, M32307, M32507 and M32607). ELISA plates are quantitated using Molecular Devices Versamax reader at 450 nM. The group mean titer of each antibody analyte is converted to percent of vehicle control (=100%).

Example H

Adoptive Transfer Experimental Autoimmune Encephalomyelitis

The effect of a compound of Formula I on an autoimmune disease induced by T cells can be determined using an adoptive transfer EAE model, an animal model of human multiple sclerosis (Brain (2006), 129, 1953-1971). This model relies on the injection of T cells from animals with EAE into disease-free host animals. This injection of cells is known to those skilled in the art as adoptive transfer. By injecting the animals with activated, encephalogenic T cells, this model is focused on the pathogenic stage of EAE autoimmune disease. On Day −14, C57BL/6 mice (Taconic Farms; 10 weeks old) are immunized with a disease-causing protein, MOG(35-55) peptide in complete Freund's adjuvant (Hooke Laboratories, catalog #EK-0113). On Day −3, spleens are harvested, single cell suspensions are prepared and then 5,000,000 cells/mL are stimulated with 20 μg/mL MOG(33-55) peptide (Open Biosystems), 30 ng/mL IL-12 (R&D Systems catalog #419-ML-010), 10 μg/mL anti-IFNγ antibody (BD Biosciences catalog #554408) at 37° C., 5% $CO_2$. On Day 0, 1,500,000 of these cells are injected intravenously into the tail veins of C57BL/6 recipient mice. The recipient mice are divided into treatment groups for vehicle (distilled water; 10 mL/kg) or the compound of Formula I (200 mg/kg), both administered by oral gavage twice daily for 26 days. The recipient mice are scored daily days 0 through 26 using the following clinical scoring system:

0.0—no symptoms
    1.0—limp tail
    2.0—limp tail and weakness of hind legs
    3.0—limp tail and complete hind limb paralysis, or partial front and hind limb paralysis, or severe head tilting combined with pushing against cage wall and spinning when picked up by tail
    4.0—limp tail, complete hind limb paralysis and partial front limb paralysis
    5.0—Full body paralysis, or spontaneous rolling or found dead due to paralysis Example I MOG(35-55)-Induced Experimental Autoimmune Encephalomyelitis An additional method of determining the effect of compounds of Formula I on an autoimmune disease associated with T cells and cytokines uses the MOG-induced experimental autoimmune encephalomyelitis (EAE) model. MOG-induced EAE is an animal model of human multiple sclerosis (Brain (2006), 129, 1953-1971).

On Day 0, C57BL/6J mice (Jackson Laboratories #000664, 6-8 weeks of age) are injected subcutaneously with 100 µL of complete Freund's adjuvant (CFA) prepared as a 1:1 emulsion of (a) incomplete Freund's adjuvant (Difco, catalog #263910) containing 8 mg/mL *M. tuberculosis* H37RA (Difco, catalog #231141) and (b) phosphate buffered saline (PBS) containing 1 mg/mL MOG(35-55) peptide (California Peptide Research Inc). On the day 0 and 2, mice are injected intravenously with 200 ng of pertussis toxin (List Biological Laboratories, catalog #181). On day 7, the mice are randomized into treatment groups which received vehicle (distilled water) or the compound of Formula I (200 mg/kg) administered by oral gavage twice daily from days 7 through 27.

The mice are scored daily on days 7 through 37 using the following clinical scoring system:

0.0—no symptoms
    0.5—tail weakness
    1.0—limp tail
    1.5—unsteady gait, mild hind limb ataxia
    2.0—partial hind limb paralysis (hind limbs carrying weight)
    2.5—partial hind limb paralysis (hind limbs not carrying weight)
    3.0—full hind limb paralysis
    3.5—full hind limb paralysis and partial front limb paralysis
    4.0—full body paralysis Example J CD4+CD45RBhi Adoptive Transfer Inflammatory Bowel Disease The following adoptive transfer model of inflammatory bowel disease (IBD) can be performed to determine the effect of compounds of Formula I on IBD, which is an autoimmune disease associated with T cells and cytokines On Day 0, CD4+ T cells are isolated from the spleens of female Balb/cAnNCrl mice (Charles River Laboratories; 12 weeks old) as described in Example E. The resulting cells are labeled with fluorescent antibodies against CD4 and CD45 markers and are sorted by flow cytometry for CD4+ CD45RBhi cells based on fluorescence. 400,000 CD4+ CD45RBhi cells are then injected intraperitoneally into C.B17/Icr-Prkdc$^{scid}$/IcrIcoCrl mice (Charles River Laboratories strain code 236; 12 weeks old). This injection of cells is known to those skilled in the art as "adoptive transfer". On Day 21, mice are randomized into groups for oral gavage treatment with vehicle (1% carboxymethylcellulose sodium (CMC)/0.5% Tween 80 once daily; CMC, Sigma catalog #C9481, Tween 80 Sigma catalog #P1754) or the compound of Formula I (200 mg/kg; twice daily). Treatments continued through Day 42.

At the conclusion of the study, mice are sacrificed and the distal half of their colons are placed in 10% neutral buffered formalin (Richard Allen Scientific catalog #53120-1) and paraffin embedded, sectioned into 4 µm slices and stained with hematoxylin and eosin (H&E) for analysis by a board certified veterinary pathologist.

For each H&E stained section, submucosal edema is quantitated by measuring the distance from the muscularis mucosa to the internal border of the outer muscle layer in a non-tangential area thought to most representative the severity of this change. Mucosal thickness is also measured in a non-tangential area of the section that best represented the overall mucosal thickness. This parameter is indicative of gland elongation and mucosal hyperplasia. The extent of inflammation (macrophage, lymphocyte and polymorphonuclear leukocyte (PMN) infiltrate) is assigned severity scores according to the following criteria:

Normal=0
    Minimal=1 (generally focal affecting 1-10% of mucosa or if diffuse then minimal)
    Mild=2 (generally focal affecting 11-25% of mucosa or if diffuse then mild)
    Moderate=3 (26-50% of mucosa affected with areas of gland loss replaced by inflammatory cell infiltrate, milder in remaining areas of mucosa)
    Marked=4 (51-75% of mucosa affected with areas of gland loss replaced by inflammatory cell infiltrate, milder in remaining areas of mucosa)
    Severe=5 (76-100% of mucosa affected with areas of gland loss replaced by inflammatory cell infiltrate, milder in remaining areas of mucosa)

The parameters reflecting epithelial cell loss/damage are scored individually using a % area involved scoring method:

None=0
    1-10% of the mucosa affected=1
    11-25% of the mucosa affected=2
    26-50% of the mucosa affected=3
    51-75% of the mucosa affected=4
    76-100% of the mucosa affected=5

Parameters that are scored using % involvement included: colon glandular epithelial loss (this includes crypt epithelial as well as remaining gland epithelial loss), and colon erosion (this reflects loss of surface epithelium and generally is associated with mucosal hemorrhage (reflective of the bleeding seen clinically and at necropsy).

The three scored parameters (inflammation, glandular epithelial loss, and erosion) are ultimately summed to arrive at a sum of histopathology scores, which indicates the overall damage and would have a maximum score of 15.

Example K

MRL/lpr Lupus Model

MRL/lpr is considered to be an animal model of systemic lupus erythematosus (SLE), an autoimmune disease (Cohen and Maldonado 2003, Current Protocols in Immunology Chapter 15, Unit 15.20). MRL/lpr mice have a defect in the apoptosis of activated lymphocytes and over time develop a spontaneous and severe lymphoproliferative disorder characterized by enlarged lymphoid organs, auto-antibody production and kidney disease resulting in proteinuria. SLE patients also exhibit auto-antibodies, and some patients develop kidney disease. To determine the effect of compounds of Formula I in this model of SLE, the following experiment can be conducted.

MRL/MpJ-Fas<lpr> and age-matched MRL/MpJ control mice (Jackson Laboratories, catalog #000485 and #000486, respectively) are treated once daily with vehicle (1% CMC/0.5% Tween 80) or twice daily with the compound of Formula I (200 mg/kg) for 10 weeks. Body weights, lymphadenopathy and urine protein levels are monitored weekly. Urine protein levels are determined with Bayer Albustix dipsticks (Bayer catalog #2191) and scored according to the following scale:
0=none detected
0.5=trace amounts
1=30 mg/dL
2=100 mg/dL
3=300 mg/dL
4=2000 mg/dL Serum levels of anti-ds-DNA antibody are measured by ELISA (Alpha Diagnostic, catalog #5120) on Day 28 and upon study termination. ELISA plates are quantitated using a Molecular Devices Versamax plate reader at 450 nM and titers calculated relative using to a standard curve using a 4-parameter curve fit with Softmax Pro software.

Example 1

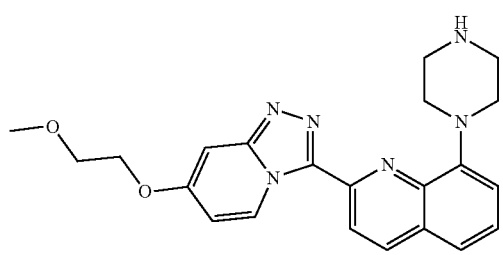 [SMILES: COCCOc1ccn2c(-c3ccc4cccc(N5CCNCC5)c4n3)nnc2c1]

2-(7-(2-Methoxyethoxy)-[1,2,4]triazolo[4,3-a]pyridin-3-yl)-8-(piperazin-1-yl)quinoline

Step A: Preparation of 2-chloro-4-(2-methoxyethoxy)pyridine

Potassium 2-methylpropan-2-olate (4.214 g, 35.678 mmol) was slowly added under an atmosphere of dry $N_2$ to a solution of 2-chloro-4-nitropyridine (5.142 g, 32.434 mmol) in 2-methoxyethanol (40.0 mL, 506.74 mmol). The reaction was stirred at ambient temperature for 2 hours and then concentrated under reduced pressure. The resulting oil was diluted with water (200 mL) and extracted with EtOAc. The combined organic phases were dried over $Na_2SO_4$, filtered and concentrated under reduced pressure to give 5.36 g (88%) of desired product as a colorless oil.

Step B: Preparation of 2-hydrazinyl-4-(2-methoxyethoxy)pyridine

Hydrazine (10 mL, 318.6 mmol) was added to a solution of 2-chloro-4-(2-methoxyethoxy)pyridine (1.00 g, 5.330 mmol) in pyridine (25 mL). The reaction was heated to reflux. After 18 hours the reaction mixture was partitioned between $H_2O$ and DCM and the aqueous phase was extracted with DCM. The combined organic extracts were dried over $Na_2SO_4$, filtered and concentrated under reduced pressure. The residue was purified via flash column chromatography (40:1 DCM/MeOH followed by 20:1 DCM/MeOH) to provide 320 mg (33%) of desired product as a white solid.

Step C: Preparation of 8-(tert-butyldimethylsilyloxy)quinoline-2-carbaldehyde 8-Hydroxyquinoline-2-carbaldehyde (5.00 g, 28.9 mmol) and imidazole (4.32 g, 63.5 mmol) were dissolved in DCM (50 mL) under $N_2$. The reaction mixture was cooled to 0° C. after which time tert-butylchlorodimethylsilane (4.94 g, 31.8 mmol) was added. After stirring for 16 hours at ambient temperature, the reaction mixture was partitioned between DCM and $H_2O$. The organic layer was washed with $H_2O$ and aqueous saturated $NaHCO_3$, dried over $Na_2SO_4$, filtered and concentrated under reduced pressure to afford an orange oil. The residue was purified via flash column chromatography (10:1 Hexane/EtOAc) to provide 6.85 g (83%) of desired product as a yellow/orange oil.

Step D: Preparation of (E)-8-(tert-butyldimethylsilyloxy)-2-((2-(4-(2-methoxyethoxy)pyridin-2-yl)hydrazono)methyl)quinoline 2-Hydrazinyl-4-(2-methoxyethoxy)pyridine (0.076 g, 0.415 mmol) and 8-(tert-butyldimethylsilyloxy)quinoline-2-carbaldehyde (0.119 g, 0.415 mmol) were heated to reflux in EtOH (2 mL) for 16 hours. After cooling to ambient temperature the reaction mixture was filtered and washed with EtOH to provide 105 mg (56%) of desired product as an orange solid.

Step E: Preparation of 8-(tert-butyldimethylsilyloxy)-2-(7-(2-methoxyethoxy)-[1,2,4]triazolo[4,3-a]pyridin-3-yl)quinoline To a solution of (E)-8-(tert-butyldimethylsilyloxy)-2-((2-(4-(2-methoxyethoxy)pyridin-2-yl)hydrazono)methyl)quinoline (0.101 g, 0.223 mmol) in DCM (1.0 mL) was added iodosobenzene diacetate (0.0719 g, 0.223 mmol). After stirring at ambient temperature for 5 hours the reaction mixture was partitioned between DCM and aqueous saturated $Na_2S_2O_3$. The organic layer was washed with brine, dried over $Na_2SO_4$, filtered and concentrated under reduced pressure. The residue was purified via flash column chromatography (40:1 DCM/MeOH) to provide 70 mg (70%) of desired product.

Step F: Preparation of 2-(7-(2-methoxyethoxy)-[1,2,4]triazolo[4,3-a]pyridin-3-yl)quinolin-8-ol To a solution of 8-(tert-butyldimethylsilyloxy)-2-(7-(2-methoxyethoxy)-[1,2,4]triazolo[4,3-a]pyridin-3-yl)quinoline (0.070 g, 0.155 mmol) in THF (8 mL) was added 1M HCl (1.5 mL, 1.50 mmol). After stirring at ambient temperature for 2 hours 1 M HCl (5 mL) was added and the reaction mixture stirred for a further 16 hours. The mixture was neutralized with 1M NaOH and diluted with EtOAc. The organic layer was washed with brine, dried over $Na_2SO_4$, filtered and concentrated under reduced pressure to give 40 mg (77%) of desired product.

Step G: Preparation of 2-(7-(2-methoxyethoxy)-[1,2,4]triazolo[4,3-a]pyridin-3-yl)quinolin-8-yl trifluoromethanesulfonate 2-(7-(2-M ethoxyethoxy)-[1,2,4]triazolo[4,3-a]pyridin-3-yl)quinolin-8-ol (0.040 g, 0.119 mmol), N-phenyltriflimide (0.0467 g, 0.131 mmol) and TEA (0.0365 mL, 0.262 mmol) were dissolved in a solution of 2.5:1 THF/DMF (0.60 mL) under $N_2$ atmosphere. After stirring at ambient temperature for 3 hours, the reaction mixture was diluted with $H_2O$ and the resulting precipitate was filtered to give 27 mg (49%) of desired product.

Step H: Preparation of tert-butyl 4-(2-(7-(2-methoxyethoxy)-[1,2,4]triazolo[4,3-a]pyridin-3-yl)quinolin-8-yl)piperazine-1-carboxylate 2-(7-(2-methoxyethoxy)-[1,2,4]triazolo[4,3-a]pyridin-3-yl)quinolin-8-yl trifluoromethane sulfonate (0.027 g, 0.0576 mmol), tert-butyl piperazine-1-carboxylate (0.0215 g, 0.115 mmol), $Cs_2CO_3$ (0.0282 g, 0.0865 mmol), $Pd_2\,dba_3$ (0.00528 g, 0.00576 mmol) and Binap-rac (0.00718 g, 0.0115 mmol) were combined in toluene (0.5 mL) in a sealed vial. The reaction mixture was stirred at 100° C. for 16 hours then concentrated under reduced pressure. The resulting residue was diluted with EtOAc, washed with aqueous saturated $NaHCO_3$ and brine, dried over $Na_2SO_4$, filtered and concentrated under reduced pressure to an orange solid. Purification via flash column chromatography (40:1 DCM/MeOH followed by 20:1 DCM/MeOH) provided 22 mg (76%) of desired product.

Step I: Preparation of 2-(7-(2-methoxyethoxy)-[1,2,4]triazolo[4,3-a]pyridin-3-yl)-8-(piperazin-1-yl)quinoline To a solution of tert-butyl 4-(2-(7-(2-methoxyethoxy)-[1,2,4]triazolo[4,3-a]pyridin-3-yl)quinolin-8-yl)piperazine-1-carboxylate (0.022 g, 0.0436 mmol) in THF/MeOH (1 mL) was added 4 M HCl (0.109 mL, 0.436 mmol) in dioxane. The reaction mixture was stirred at ambient temperature for 16 hours then neutralized with 1 M NaOH and extracted with EtOAc. The combined organic layers were washed with brine, dried over $Na_2SO_4$, filtered and concentrated under reduced pressure. The residue was purified via flash column chromatography (40:1 DCM/MeOH followed by 10:1 DCM/MeOH) to provide 4 mg (23%) of desired product as a yellow solid. MS APCI (+) m/z 405.4 (M+1) detected.

Example 2

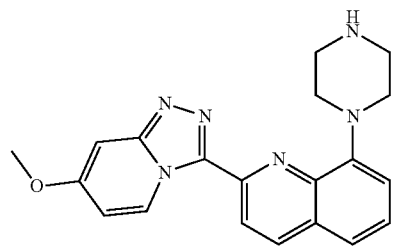 [SMILES: COc1ccn2c(-c3ccc4cccc(N5CCNCC5)c4n3)nnc2c1]

2-(7-Methoxy-[1,2,4]triazolo[4,3-a]pyridin-3-yl)-8-(piperazin-1-yl)quinoline

Prepared as described in Example 1 using methanol in place of 2-methoxyethanol in step A. MS APCI (+) m/z 361.3 (M+1) detected.

Example 3

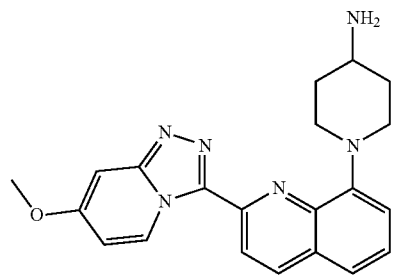 [SMILES: COc1ccn2c(-c3ccc4cccc(N5CCC(N)CC5)c4n3)nnc2c1]

1-(2-(7-Methoxy-[1,2,4]triazolo[4,3-a]pyridin-3-yl)quinolin-8-yl)piperidin-4-amine Prepared as described in Example 1 using 2-chloro-4-methoxypyridine in place of 2-chloro-4-(2-methoxyethoxy)pyridine in step B, and substituting tert-butyl piperidin-4-ylcarbamate for tert-butyl piperazine-1-carboxylate in step H. MS APCI (+) m/z 375.2 (M+1) detected.

Example 4

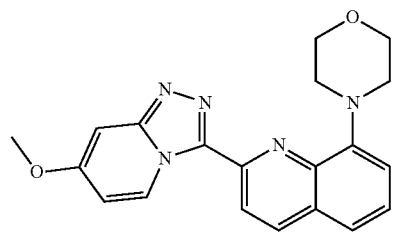 [SMILES: COc1ccn2c(-c3ccc4cccc(N5CCOCC5)c4n3)nnc2c1]

4-(2-(7-Methoxy-[1,2,4]triazolo[4,3-a]pyridin-3-yl)quinolin-8-yl)morpholine

Prepared as described in Example 1 using 2-chloro-4-methoxypyridine in place of 2-chloro-4-(2-methoxyethoxy)

pyridine in step B, and substituting morpholine for tert-butyl piperazine-1-carboxylate in step H. MS APCI (+) m/z 362.3 (M+1) detected.

Example 5

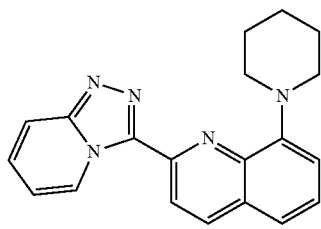 [SMILES: c1cc(N2CCCCC2)c2nc(-c3nnc4ccccn34)ccc2c1]

2-([1,2,4]-Triazolo[4,3-a]pyridin-3-yl)-8-(piperidin-1-yl)quinoline

Prepared as described in Example 1 using 2-chloropyridine as a replacement for 2-chloro-4-(2-methoxyethoxy)pyridine in step B, and substituting piperidine for tert-butyl piperazine-1-carboxylate in step H. MS ESI (+) m/z 330 (M+1) detected.

Example 6

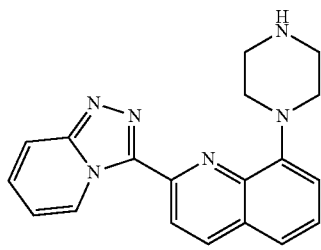 [SMILES: c1cc(N2CCNCC2)c2nc(-c3nnc4ccccn34)ccc2c1]

2-([1,2,4]-Triazolo[4,3-a]pyridin-3-yl)-8-(piperazin-1-yl)quinoline

Prepared as described in Example 1 using 2-chloropyridine as a replacement for 2-chloro-4-(2-methoxyethoxy)pyridine in step B. MS ESI (+) m/z 331 (M+1) detected.

Example 7

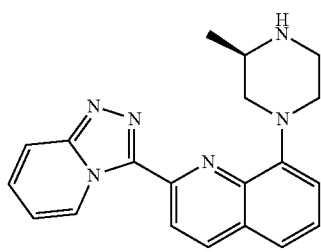 [SMILES: C[C@@H]1CN(c2cccc3ccc(-c4nnc5ccccn45)nc23)CCN1]

(R)-2-([1,2,4]Triazolo[4,3-a]pyridin-3-yl)-8-(3-methylpiperazin-1-yl)quinoline

Prepared as described in Example 1 using 2-chloropyridine as a replacement for 2-chloro-4-(2-methoxyethoxy)pyridine in step B, and substituting (R)-tert-butyl 2-methylpiperazine-1-carboxylate for tert-butyl piperazine-1-carboxylate in step H. MS ESI (+) m/z 345 (M+1) detected.

Example 8

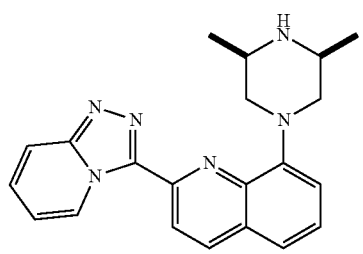 [SMILES: C[C@@H]1CN(c2cccc3ccc(-c4nnc5ccccn45)nc23)C[C@H](C)N1]

2-([1,2,4]Triazolo[4,3-a]pyridin-3-yl)-8-((cis)-3,5-dimethylpiperazin-1-yl)quinoline Prepared as described in Example 1 using 2-chloropyridine as a replacement for 2-chloro-4-(2-methoxyethoxy)pyridine in step B, and substituting (cis)-tert-butyl 2,6-dimethylpiperazine-1-carboxylate for tert-butyl piperazine-1-carboxylate in step H. MS ESI (+) m/z 359 (M+1) detected.

Example 9

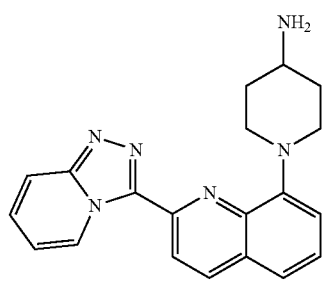 [SMILES: NC1CCN(c2cccc3ccc(-c4nnc5ccccn45)nc23)CC1]

1-(2-([1,2,4]Triazolo[4,3-a]pyridin-3-yl)quinolin-8-yl)piperidin-4-amine

Prepared as described in Example 1 using 2-chloropyridine as a replacement for 2-chloro-4-(2-methoxyethoxy)pyridine in step B, and substituting tert-butyl piperidin-4-ylcarbamate for tert-butyl piperazine-1-carboxylate in step H. MS ESI (+) m/z 345 (M+1) detected.

Example 10

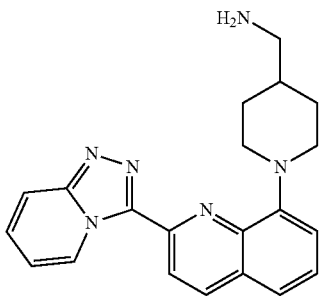 [SMILES: NCC1CCN(c2cccc3ccc(-c4nnc5ccccn45)nc23)CC1]

(1-(2-([1,2,4]Triazolo[4,3-a]pyridin-3-yl)quinolin-8-yl)piperidin-4-yl)methanamine Prepared as described in Example 1 using 2-chloropyridine as a replacement for 2-chloro-4-(2-methoxyethoxy)pyridine in step B, and substituting tert-butyl piperidin-4-ylmethylcarbamate for tert-butyl piperazine-1-carboxylate in step H. MS ESI (+) m/z 359 (M+1) detected.

Example 11

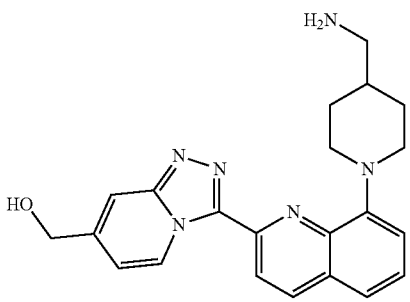 [SMILES: NCC1CCN(c2cccc3ccc(-c4nnc5cc(CO)ccn45)nc23)CC1]

(3-(8(4-(Aminomethyl)piperidin-1-yl)quinolin-2-yl)-[1,2,4]triazolo[4,3-a]pyridin-7-yl)methanol

Step A: Preparation of 8-bromo-2-vinylquinoline

To 2,8-dibromoquinoline (1.836 g, 6.398 mmol) in THF/IPA (20 mL/10 mL) was added vinylborate (0.9428 g, 7.038 mmol) and triethylamine (0.7769 g, 7.678 mmol). The reaction mixture was purged with $N_2$, and $PdCl_2$(dppf) dichloromethane adduct (0.3685 g, 0.4479 mmol) was added. The reaction was stirred at 55° C. for 12 hours, then cooled to ambient temperature. The reaction mixture was diluted with EtOAc/$H_2O$, and the organic layer was separated and concentrated to provide the crude product.

Step B: Preparation of 1-(8-bromoquinolin-2-yl)ethane-1,2-diol

To 8-bromo-2-vinylquinoline (0.886 g, 3.78 mmol) in acetone/$H_2O$ (8 mL/2 mL) was added 4-methylmorpholine N-oxide (1.06 g, 4.54 mmol) followed by $OsO_4$ (0.5 mL, 2.5% in t-BuOH). The reaction mixture was stirred for two hours at ambient temperature then diluted with dichloromethane. The organic layer was washed with saturated sodium sulfate and brine and concentrated to give crude product.

Step C: Preparation of 8-bromo-2-(2,2-dimethyl-1,3-dioxolan-4-yl)quinoline

To 1-(8-bromoquinolin-2-yl)ethane-1,2-diol (505 mg, 1.88 mmol) in acetone (5 mL) and 2,2-dimethoxypropane (5 mL, 1.88 mmol) was added Montmorillonite K 10 (1 g). The reaction mixture was stirred for 2 hours, then filtered and concentrated to give crude product.

Step D: Preparation of tert-butyl (1-(2-(2,2-dimethyl-1,3-dioxolan-4-yl)quinolin-8-yl)piperidin-4-yl)methylcarbamate To 8-bromo-2-(2,2-dimethyl-1,3-dioxolan-4-yl)quinoline (101 mg, 0.328 mmol) in toluene (1.3 mL) was added tert-butyl piperidin-4-ylmethylcarbamate (84.3 mg, 0.393 mmol), Pd(OAc)$_2$ (7.3 mg, 0.033 mmol), Binap-rac (25 mg, 0.039 mmol) and $Cs_2CO_3$ (235 mg, 0.721 mmol). The reaction was purged twice with nitrogen and heated at reflux overnight. The reaction mixture was cooled to ambient temperature and filtered through Celite, and the solids were washed with EtOAc (20 mL). The filtrate was concentrated, and the crude material was purified by silica gel chromatography (EtOAc/Hexane 1:6) provided final product.

Step E: Preparation of tert-butyl (1-(2-(1,2-dihydroxyethyl)quinolin-8-yl)piperidin-4-yl)methylcarbamate To tert-butyl (1-(2-(2,2-dimethyl-1,3-dioxo lan-4-yl)quinolin-8-yl)piperidin-4-yl)methylcarbamate (81 mg, 0.18 mmol) in THF (3 mL) was added HCl (20 mg, 0.55 mmol) (6M). The reaction was stirred for 3 hours at ambient temperature and then diluted with EtOAc (10 mL) and saturated $NaHCO_3$ (5 mL). The phases were separated, and the organic layer was dried and concentrated to give crude product.

Step F: Preparation of tert-butyl (1-(2-formylquinolin-8-yl)piperidin-4-yl)methylcarbamate Sodium periodate (0.34 mL, 0.22 mmol was added dropwise to a slurry of silica gel (0.4 g) in DCM (3 mL)). The reaction was stirred for 10 minutes. tert-Butyl (1-(2-(1,2-dihydroxyethyl)quinolin-8-yl)piperidin-4-yl)methylcarbamate (74 mg, 0.18 mmol) in DCM (2 mL) was then added to the slurry and the reaction was stirred for 30 minutes. The reaction was filtered and the collected solids were washed with DCM (20 mL). The filtrate was concentrated to give the crude product.

Step G: Preparation of (E)-tert-butyl (1-(2-((2-(4-iodopyridin-2-yl)hydrazono)methyl)quinolin-8-yl)piperidin-4-yl)methylcarbamate To tert-butyl (1-(2-formylquinolin-8-yl)piperidin-4-yl)methylcarbamate (112 mg, 0.303 mmol) in DCM (20 mL) was added 1-(4-iodopyridin-2-yl)hydrazine (78.4 mg, 0.333 mmol). The reaction mixture was stirred for 1 hour and then taken on to directly to the next step.

Step H: Preparation of tert-butyl (1-(2-(7-iodo-[1,2,4]triazolo[4,3-a]pyridin-3-yl)quinolin-8-yl)piperidin-4-yl)methylcarbamate To (E)-tert-butyl (1-(2-((2-(4-iodopyridin-2-yl)hydrazono)methyl)quinolin-8-yl)piperidin-4-yl)methylcarbamate (178 mg, 0.304 mmol) was added iodobenzene diacetate (IBD) (127 mg, 0.395 mmol). The reaction was stirred for 2 hours. Additional IBD (0.5 eq) was added and the reaction was stirred for another 2 hours and then quenched with saturated Na$_2$S$_2$O$_3$ (5 mL). The organic layer was extracted with DCM, dried (Na$_2$SO$_4$) and concentrated. The crude material was purified by silica gel chromatography (EtOAc/Hexane/MeOH 2:1:0.1) to provide the final product.

Step I: Preparation of tert-butyl (1-(2-(7-vinyl-[1,2,4] triazolo[4,3-a]pyridin-3-yl)quinolin-8-yl)piperidin-4-yl)methylcarbamate To tert-butyl (1-(2-(7-iodo-[1,2,4]triazolo[4,3-a]pyridin-3-yl)quinolin-8-yl)piperidin-4-yl)methylcarbamate (91 mg, 0.16 mmol) in THF/IPA (2/1 mL) was added C$_2$H$_3$BF$_3$K (31 mg, 0.23 mmol), PdCl$_2$(dppf) dichloromethane adduct (13 mg, 0.016 mmol) and triethylamine (24 mg, 0.23 mmol). The reaction was stirred for 2 hours, and then heated at 60° C. overnight. The reaction was cooled to ambient temperature and concentrated. The crude material was purified by silica gel chromatography (20:1 Hexane/EtOAc) to provide the final product.

Step J: Preparation of tert-butyl (1-(2-(7-(1,2-dihydroxyethyl)-[1,2,4]triazolo[4,3-a]pyridin-3-yl)quinolin-8-yl)piperidin-4-yl)methylcarbamate To tert-butyl (1-(2-(7-vinyl-[1,2,4]triazolo[4,3-a]pyridin-3-yl)quinolin-8-yl)piperidin-4-yl)methylcarbamate (68 mg, 0.14 mmol) in acetone (2 mL) was added OsO$_4$ (178 mg, 0.014 mmol) (2% in tBuOH) and 4-methylmorpholine N-oxide (49 mg, 0.21 mmol) (50% in H$_2$O). The reaction was stirred for 2 hours and then concentrated. The crude material was purified by silica gel chromatography (20:1 Hexane/EtOAc) to provide the final product.

Step K: Preparation of tert-butyl (1-(2-(7-formyl-[1,2,4]triazolo[4,3-a]pyridin-3-yl)quinolin-8-yl)piperidin-4-yl)methylcarbamate To a slurry of silica gel (0.1 g) in DCM (3 mL) was added sodium periodate (0.13 mL, 0.087 mmol). The reaction was stirred for 10 minutes. tert-Butyl (1-(2-(7-(1,2-dihydroxyethyl)-[1,2,4]triazolo[4,3-a]pyridin-3-yl)quinolin-8-yl)piperidin-4-yl)methylcarbamate (30 mg, 0.058 mmol) in DCM (2 mL) was then added to the slurry. The reaction was stirred for 30 minutes, then filtered and washed with DCM (20 mL). The organic layer was concentrated to give crude product.

Step L: Preparation of tert-butyl(1-(2-(7-(hydroxymethyl)-[1,2,4]triazolo[4,3-a]pyridin-3-yl)quinolin-8-yl)piperidin-4-yl)methylcarbamate To tert-butyl (1-(2-(7-formyl-[1,2,4]triazolo[4,3-a]pyridin-3-yl)quinolin-8-yl)piperidin-4-yl)methylcarbamate (10 mg, 0.021 mmol) in DCM/MeOH (1 mL/1 mL) was added NH$_3$ in IPA (0.1 mL, 2M) and HOAc (0.2 mL), followed by NaB(OAc)$_3$H (13 mg, 0.062 mmol). The reaction was stirred for 5 hours and then concentrated. The crude material was purified by silica gel chromatography (DCM/MeOH/NH$_4$OH 20:1:0.1) to provide the desired product (3 mg). MS ESI (+) m/z 489 (M+1) detected.

Step M: Preparation of (3-(8-(4-(Aminomethyl)piperidin-1-yl)quinolin-2-yl)-[1,2,4]triazolo[4,3-a]pyridin-7-yl)methanol Prepared from tert-butyl(1-(2-(7-(hydroxymethyl)-[1,2,4]triazolo[4,3-a]pyridin-3-yl)quinolin-8-yl)piperidin-4-yl)me-thylcarbamate according to the method of Example 1 (Step I). MS ESI (+) m/z 389 (M+1) detected.

Example 12

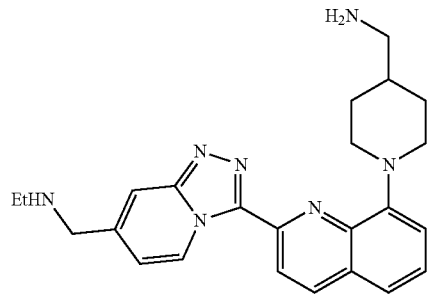

N-((3-(8-(4-(aminomethyl)piperidin-1-yl)quinolin-2-yl)-[1,2,4]triazolo[4,3-a]pyridin-7-yl)methyl)ethanamine Step A: Preparation of tert-butyl (1-(2-(7-((ethylamino)methyl)-[1,2,4]triazolo[4,3-a]pyridin-3-yl) quinolin-8-yl)piperidin-4-yl)methylcarbamate To tert-butyl (1-(2-(7-formyl-[1,2,4]triazolo[4,3-a]pyridin-3-yl)quinolin-8-yl)piperidin-4-yl)methylcarbamate (Example 11, steps A-K; 10 mg, 0.021 mmol) in DCM/MeOH (1 mL/1 mL) was added EtNH$_2$ (0.1 mL, 2M in THF) and HOAc (0.2 mL), followed by NaB(OAc)$_3$H (13 mg, 0.062 mmol). The reaction mixture was stirred for 5 hours at ambient temperature and then concentrated. The crude material was purified by silica gel chromatography (DCM/MeOH/NH$_4$OH 20:1:0.1) to provide the desired product (4 mg). MS APCI (+) m/z 343 (M+1) detected.

Step B: Preparation of N-((3-(8-(4-(aminomethyl) piperidin-1-yl)quinolin-2-yl)-[1,2,4]triazolo[4,3-a] pyridin-7-yl)methyl)ethanamine Prepared from tert-butyl (1-(2-(7-((ethylamino)methyl)-[1,2,4]triazolo[4,3-a]pyridin-3-yl)quinolin-8-yl)piperidin-4-yl)methylcarbamate as described in Example 1 (step I). MS ESI (+) m/z 416 (M+1) detected.

Example 13

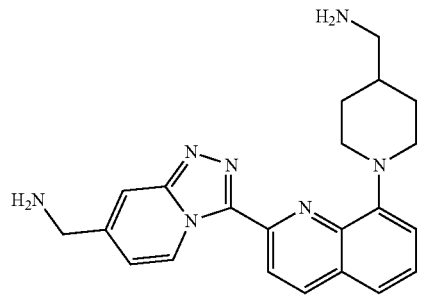 [SMILES: NCc1ccn2c(-c3ccc4cccc(N5CCC(CN)CC5)c4n3)nnc2c1]

(1-(2-(7-(Aminomethyl)-[1,2,4]triazolo[4,3-a]pyridin-3-yl)quinolin-8-yl)piperidin-4-yl)methanamine Prepared as described in Example 12 using NH₃ in replacement of EtNH₂. MS ESI (+) m/z 388 (M+1) detected.

Example 14

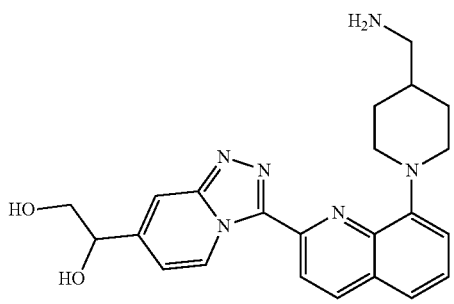 [SMILES: NCC1CCN(c2cccc3ccc(-c4nnc5cc(C(O)CO)ccn45)nc23)CC1]

1-(3-(8-(4-(Aminomethyl)piperidin-1-yl)quinolin-2-yl)-[1,2,4]triazolo[4,3-a]pyridin-7-yl)ethane-1,2-diol Step A: Preparation of tert-butyl (1-(2-formylquinolin-8-yl)piperidin-4-yl)methylcarbamate Prepared as described in Example 1, Step H, substituting 8-bromoquinoline-2-carbaldehyde for 2-(7-(2-methoxyethoxy)-[1,2,4]triazolo[4,3-a]pyridin-3-yl)quinolin-8-yl trifluoromethane sulfonate, and tert-butyl piperidin-4-ylmethylcarbamate for tert-butyl piperazine-1-carboxylate.

Step B: Preparation of tert-butyl (1-(2-((2-(4-iodopyridin-2-yl)hydrazono)methyl)quinolin-8-yl)piperidin-4-yl)methylcarbamate Prepared as described in Example 1, steps D-E, using tert-butyl (1-(2-formylquinolin-8-yl)piperidin-4-yl)methylcarbamate in place of 8-(tert-butyldimethylsilyloxy)quinoline-2-carbaldehyde, and 2-hydrazinyl-4-iodopyridine in place of 2-Hydrazinyl-4-(2-methoxyethoxy)pyridine.

Step C: Preparation of tert-butyl (1-(2-(7-vinyl-[1,2,4]triazolo[4,3-a]pyridin-3-yl)quinolin-8-yl)piperidin-4-yl)methylcarbamate To tert-butyl (1-(2-(7-iodo-[1,2,4]triazolo[4,3-a]pyridin-3-yl)quinolin-8-yl)piperidin-4-yl)methylcarbamate (91 mg, 0.16 mmol) in THF/IPA (2/1 mL) was added C₂H₃BF₃K (31 mg, 0.23 mmol), PdCl₂(dppf) dichloromethane adduct (13 mg, 0.016 mmol) and triethylamine (24 mg, 0.23 mmol). The reaction was stirred for 2 hours, followed by heating at 60° C. overnight. The reaction was then cooled to ambient temperature and concentrated, and the residue was purified by flash column chromatography (20:1 Hexane/EtOAc) providing the desired product (90% yield; 0.068 g).

Step D: Preparation of tert-butyl (1-(2-(7-(1,2-dihydroxyethyl)-[1,2,4]triazolo[4,3-a]pyridin-3-yl)quinolin-8-yl)piperidin-4-yl)methylcarbamate To tert-butyl (1-(2-(7-vinyl-[1,2,4]triazolo[4,3-a]pyridin-3-yl)quinolin-8-yl)piperidin-4-yl)methylcarbamate (68 mg, 0.14 mmol) in acetone (2 mL) was added OsO₄ (178 mg, 0.014 mmol) (2% in tBuOH) and NMO (49 mg, 0.21 mmol) (50% in H₂O). The reaction was then stirred for 2 hours, then concentrated and purified by flash column chromatography (20:1 Hexane/EtOAc), affording the desired product.

Step D: Preparation of 1-(3-(8-(4-(Aminomethyl)piperidin-1-yl)quinolin-2-yl)-[1,2,4]triazolo[4,3-a]pyridin-7-yl)ethane-1,2-diol To tert-butyl (1-(2-(7-(1,2-dihydroxyethyl)-[1,2,4]triazolo[4,3-a]pyridin-3-yl)quinolin-8-yl)piperidin-4-yl)methylcarbamate (2 mg, 0.004 mmol) in DCM (1 mL) was added TFA (0.5 mL). The reaction was then stirred for 1 hour, then concentrated and purified by flash column chromatography (DCM/MeOH/NH₄OH 20:1:0.1), affording the final product as a white solid (0.002 g; quantitative yield). MS ESI (+) m/z 419 (M+1) detected.

Example 15

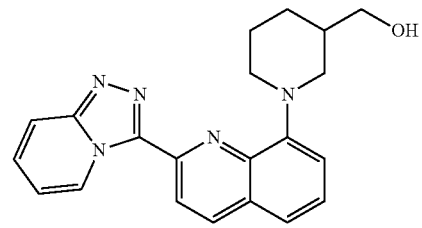 [SMILES: OCC1CCCN(c2cccc3ccc(-c4nnc5ccccn45)nc23)C1]

(1-(2-([1,2,4]Triazolo[4,3-a]pyridin-3-yl)quinolin-8-yl)piperidin-3-yl)methanol

Prepared as described in Example 1 using 2-chloropyridine as a replacement for 2-chloro-4-(2-methoxyethoxy)pyridine in step B, and piperidin-3-ylmethanol for tert-butyl piperazine-1-carboxylate in step H. MS ESI (+) m/z 360.3 (M+1) detected.

Example 16

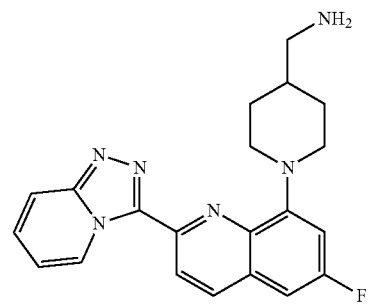 [SMILES: NCC1CCN(c2cc(F)cc3ccc(-c4nnc5ccccn45)nc23)CC1]

(1-(2-([1,2,4]triazolo[4,3-a]pyridin-3-yl)-6-fluoroquinolin-8-yl)piperidin-4-yl)methanamine Step A: Preparation of 8-bromo-6-fluoro-2-methylquinoline 2-Bromo-4-fluorobenzenamine (10 g, 52.6 mmol) was weighed into a round bottom flask, and dissolved in 40 ml of 6N HCl. The reaction mixture was then heated to reflux, followed by drop-wise addition of (E)-but-2-enal (4.578 mL, 55.3 mmol) mixed with 1.0 mL deionized water over 25 minutes. Following complete addition the reaction was heated at 100° C. for an additional 35 minutes, until all the 2-bromo-4-fluorobenzenamine had been consumed. The reaction was cooled to ambient temperature, followed by addition of 50 mL of Et$_2$O. The reaction was stirred for 5 minutes followed by removal of Et$_2$O by partitioning. The aqueous layer was replaced into the original reaction flask and ZnCl$_2$ (3.586 g, 26.3 mmol) was then added in two portions followed by cooling to 0° C. over 30 minutes. The pH of the crude reaction mixture was then adjusted to pH=8.0 using concentrated NH$_4$OH. The crude mixture was then extracted with Et$_2$O, followed by ethyl acetate. The combined organics were then dried over Na$_2$SO$_4$, and then concentrated in vacuo, affording the desired product as a brown solid (10.7 g, 85% yield). MS APCI (+) m/z 240.2 and 242.2 (M+1 of each Br isotope) detected.

Step B: Preparation of
8-bromo-2-(dibromomethyl)-6-fluoroquinoline

8-Bromo-6-fluoro-2-methylquinoline (10.7 g, 44.6 mmol) was weighed into a 1 neck flask, followed by addition of NaOAc (21.9 g, 267 mmol). The solids were suspended in 500 mL of AcOH, and the reaction heated to 70° C. Bromine (6.85 mL, 134 mmol) was the added drop-wise over 25 minutes as a solution in 30 mL of AcOH. Following complete addition, the reaction was stirred at 100° C. for 1 hour. The reaction was then cooled to ambient temperature, followed by pouring onto 750 cc of ice. The ice was allowed to melt completely and the brown slurry separated by partitioning 4×400 mL ethyl acetate. The combined organics were then dried over MgSO$_4$, and concentrated in vacuo to afford a brown solid (17.2 g, 97% yield).

Step C: Preparation of ethyl
8-bromo-6-fluoroquinoline-2-carboxylate and
8-bromo-6-fluoroquinoline-2-carboxylic acid 8-Bromo-2-(dibromomethyl)-6-fluoroquinoline (17.2 g, 43.2 mmol) was weighed into a flask and dissolved in 250 mL of EtOH, followed by addition of silver nitrate (23.5 g, 138 mmol) in 100 mL of 1:1 EtOH/H$_2$O. The reaction was heated to reflux for 1 hour, at which time all starting material had been consumed. The reaction was removed from heat and filtered hot through a medium frit scintered glass funnel, affording 5.84 g of 8-bromo-6-fluoroquinoline-2-carboxylic acid as a white/yellow powder. The mother liquor was concentrated in vacuo, followed by extractive work-up (200 mL ethyl acetate/water). The combined organics were dried over Na$_2$SO$_4$ and concentrated in vacuo to afford the desired products as an orange-brown semi solid (99% overall; 6.4 g and 5.8 g respectively). MS APCI (+) m/z 298 and 300 (M+1 of each isotope) detected; MS APCI (−) m/z 268 and 269.9 (M−1 of each Br isotope) detected.

Step D: Preparation of
(8-bromo-6-fluoroquinolin-2-yl)methanol

Ethyl 8-bromo-6-fluoroquinoline-2-carboxylate (3.201 g, 10.7 mmol) was weighed into a flask, and dissolved in 100 mL of DCM. The reaction was cooled to −78° C., followed by drop-wise addition of DIBAL-H (21.48 mL, 32.22 mmol) over 10 minutes. The reaction was then allowed to stir and warm to ambient temperature over 2 hours at which time the starting material had been consumed. The reaction was quenched with 10 mL MeOH, followed by addition of 100 mL of Rochelle's Salts, and stirred overnight to remove the emulsion. The reaction was then partitioned with ethyl acetate. The combined organic fractions were concentrated in vacuo. The crude semi solid was purified by flash column chromatography (eluting with a 20-50% ethyl acetate/hexanes gradient), affording the desired product as an orange-yellow semi solid (2.27 g, 42% yield) MS APCI (+) m/z 256.1 and 258 (M+1 of each Br isotope) detected.

Step E: Preparation of
8-bromo-6-fluoroquinoline-2-carbaldehyde (8-bromo-6-fluoroquinolin-2-yl)methanol (2 g, 7.8 mmol), DMSO (8.9 mL, 125.0 mmol), and TEA (4.9 mL, 35 mmol) were weighed into a flask and dissolved in a 10 mL of DCM, followed by cooling to 0° C. Pyridinium sulfate (4.351 g, 27.3 mmol) was added and the reaction stirred 0° C. for 1 hour. The reaction was poured onto 50 mL water and extracted with ethyl acetate. The combined organics were then dried over MgSO$_4$, then concentrated in vacuo affording a yellow/white semi-solid, which was further purified by triturating with 20% ethyl acetate/Hexanes, affording the desired product as a tan solid (1.35 g, 68% yield).

Step F: Preparation of (E)-1-((8-bromo-6-fluoro-
quinolin-2-yl)methylene)-2-(pyridin-2-yl)hydrazine 8-Bromo-6-fluoroquinoline-2-carbaldehyde (100 mg, 0.39 mmol) and 1-(pyridin-2-yl)hydrazine (43 mg, 0.39 mmol) were dissolved in 15 mL of absolute EtOH, and heated to reflux for 2 hours, at which time all starting material had been consumed. The reaction was then cooled to ambient temperature, and the yellow/orange product was collected by filtration (wash EtOH), affording (100 mg, 73.6% yield) as a yellow solid. MS APCI (+) m/z 345.1 and 347 (M+1 of each Br isotope) detected.

Step G: Preparation of 2-([1,2,4]triazolo[4,3-a]pyri-
din-3-yl)-8-bromo-6-fluoroquinoline (E)-1-((8-Bromo-6-fluoroquinolin-2-yl)methylene)-2-(pyridin-2-yl)hydrazine (100 mg, 0.290 mmol) was weighed into a 25 mL 1 neck round bottom flask and suspended in 6.0 mL of DCM, followed by addition of iodobenzene diacetate (103 mg, 0.32 mmol). The reaction was stirred at 23° C. overnight, after which all starting materials had been consumed. The reaction was transferred to a reparatory funnel and partitioned between 30 mL DCM and 30 mL Na$_2$SO$_3$, and the aqueous layer was washed with DCM. The combined organics were dried over magnesium sulfate and concentrated in vacuo to afford a white/yellow powder. The powder was triturated with 10 mL of anhydrous Et$_2$O, affording the desired product as a white solid (74 mg, 74.4% yield). MS APCI (+) m/z 343 (M+1) detected.

Step H: Preparation of tert-butyl (1-(2-([1,2,4]tria-
zolo[4,3-a]pyridin-3-yl)-6-fluoro quinolin-8-yl)pip-
eridin-4-yl)methylcarbamate 2-([1,2,4]Triazolo[4,3-a]pyridin-3-yl)-8-bromo-6-fluoroquinoline (70 mg, 0.20 mmol), tert-butyl piperidin-4-ylmethylcarbamate (56.8 mg, 0.27 mmol), and Cs$_2$CO$_3$ (66 mg, 0.20 mmol) were weighed into a 5.0 mL reaction vial and suspended in 2.0 mL of anhydrous toluene. The solution was purged with Argon followed by addition of Pd$_2$dba$_3$ (93.4 mg, 0.10 mmol), Binap-rac (12.7 mg, 0.020 mmol), then heated to 95° C. for 48 hours. The reaction was cooled to ambient temperature, followed by filtration through a celite plug to remove catalyst. The crude reaction was concentrated in vacuo and used without further purification (97 mg, 97% yield). MS APCI (+) m/z 477 (M+1) detected.

Step I: Preparation of (1-(2-([1,2,4]triazolo[4,3-a]pyridin-3-yl)-6-fluoroquinolin-8-yl)piperidin-4-yl)methanamine bis(trifluoroacetate)

tert-Butyl (1-(2-([1,2,4]triazolo[4,3-a]pyridin-3-yl)-6-fluoro quinolin-8-yl)piperidin-4-yl)methylcarbamate (97 mg, 0.204 mmol) was weighed into a flask and dissolved in 10 mL of anhydrous DCM. TFA (314 µL, 4.07 mmol) was added and the reaction was stirred at ambient temperature for 1 hour. The reaction was concentrated in vacuo, followed by trituration with anhydrous Et$_2$O, affording the desired product (43 mg, 0.114 mmol, 56.1% yield) as a yellow solid. APCI (+) m/z 377 (M+1) detected.

Example 17

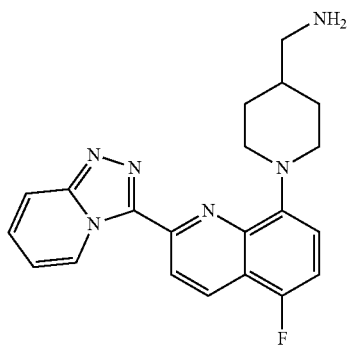 [SMILES: NCC1CCN(c2ccc(F)c3ccc(-c4nnc5ccccn45)nc23)CC1]

(1-(2-([1,2,4]triazolo[4,3-a]pyridin-3-yl)-5-fluoro-quinolin-8-yl)piperidin-4-yl)methanamine Prepared as described in Example 16 using 2-bromo-5-fluoro-aniline in place of 2-bromo-4-fluoroaniline. APCI (+) m/z 377 (M+1) detected.

Example 18

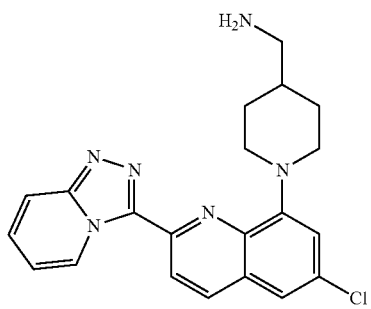 [SMILES: NCC1CCN(c2cc(Cl)cc3ccc(-c4nnc5ccccn45)nc23)CC1]

(1-(2-([1,2,4]-Triazolo[4,3-a]pyridin-3-yl)-6-chloro quinolin-8-yl)piperidin-4-yl)methanamine Prepared as previously described in Example 16 using 2-bromo-4-chloroaniline in place of 2-bromo-4-fluoro aniline. MS APCI (+) m/z 393.1 and 395.1 (M+1 of each isotope) detected.

Example 19

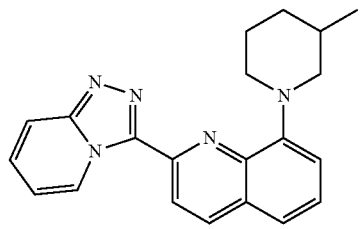 [SMILES: CC1CCCN(c2cccc3ccc(-c4nnc5ccccn45)nc23)C1]

2-([1,2,4]triazolo[4,3-a]pyridin-3-yl)-8-(3-methylpiperidin-1-yl)quinoline 2-([1,2,4]Triazolo[4,3-a]pyridin-3-yl)quinolin-8-yl trifluoromethanesulfonate (0.040 g, 0.10 mmol), 3-methylpiperidine (0.016 mL, 0.13 mmol), cesium carbonate (0.050 g, 0.15 mmol), Pd$_2$dba$_3$ (0.005 g, 0.005 mmol) and 2,2'-bis(diphenylphosphino)-1,1'-binaphthyl (0.006 g, 0.01 mmol) were added to minimal degassed toluene and heated to 92° C. overnight in a sealed tube. After stirring overnight, DCM was added, and solids removed through filtration (Waters filter), followed by concentration in vacuo. The crude mixture was then purified by flash column chromatography (gradient elution of 6% NH$_4$ in MeOH/DCM). The desired product was isolated, along with triflate starting material. The mixture was then treated with 3 N HCl aqueous at 95° C. overnight. The reaction was then cooled and solids removed by filtration. The filtrate was purified by flash column chromatography (gradient elution of 6% NH$_4$ in MeOH/DCM (Rf ~0.1 in 6% NH$_4$ in MeOH (5%) and DCM (95%)). The desired product was isolated as a yellow solid, 0.005 g (15% yield). MS ESI (+) m/z 344.3 (M+1) detected.

Example 20

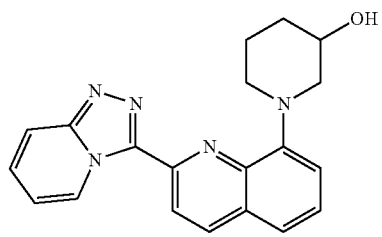 [SMILES: OC1CCCN(c2cccc3ccc(-c4nnc5ccccn45)nc23)C1]

1-(2-([1,2,4]triazolo[4,3-a]pyridin-3-yl)quinolin-8-yl)piperidin-3-ol

Prepared as described in Example 19 using piperidin-3-ol in place of 3-methylpiperidine. MS ESI (+) m/z 346.2 (M+1) detected.

Example 21

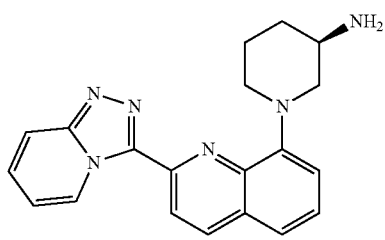 [SMILES: N[C@@H]1CCCN(c2cccc3ccc(-c4nnc5ccccn45)nc23)C1]

(R)-1-(2-([1,2,4]triazolo[4,3-a]pyridin-3-yl)quinolin-8-yl)piperidin-3-amine

Step A: Preparation of (R)-tert-butyl 1-(2-([1,2,4]triazolo[4,3-a]pyridin-3-yl)quinolin-8-yl)piperidin-3-ylcarbamate 2-([1,2,4]triazolo[4,3-a]pyridin-3-yl)quinolin-8-yl trifluoromethanesulfonate (0.040 g, 0.10 mmol), (R)-tert-butyl piperidin-3-ylcarbamate (0.026 g, 0.13 mmol), cesium carbonate (0.050 g, 0.15 mmol), Pd$_2$dba$_3$ (0.0046 g, 0.0051 mmol) and 2,2'-bis(diphenylphosphino)-1,1'-binaphthyl (0.0063 g, 0.010 mmol) were added to minimal degassed toluene and heated in a seal vial overnight at 92° C. After stirring overnight, DCM was added, solids removed through filtration (Waters filter), and the filtrate was concentrated. The crude material was purified by flash column chromatography (gradient elution of 6% NH$_4$ in MeOH/DCM). The desired product (30 mg) was isolated, as a 1:1 mixture with the triflate starting material. The mixture was used without further purification.

Step B: Preparation of (R)-1-(2-([1,2,4]triazolo[4,3-a]pyridin-3-yl)quinolin-8-yl)piperidin-3-amine (R)-tert-butyl 1-(2-([1,2,4]triazolo[4,3-a]pyridin-3-yl)quinolin-8-yl)piperidin-3-ylcarbamate (0.030 g, 0.067 mmol) was added to a 1:1 TFA-DCM and stirred for about 2 hours, at which time the reaction appeared complete by LC/TLC. The crude mixture was evaporated and purified by flash column chromatography (Horizon, using a gradient elution of 5% NH$_4$ in MeOH/DCM). The desired product was isolated as a light yellow solid (10 mg; 43% yield). MS ESI (+) m/z 345.2 (M+1) detected.

Example 22

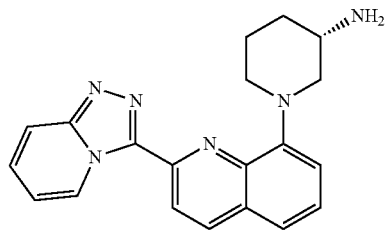 [SMILES: N[C@H]1CCCN(c2cccc3ccc(-c4nnc5ccccn45)nc23)C1]

(S)-1-(2-([1,2,4]triazolo[4,3-a]pyridin-3-yl)quinolin-8-yl)piperidin-3-amine

Prepared as described in Example 21 using (S)-tert-butyl piperidin-3-ylcarbamate in place of (R)-tert-butyl piperidin-3-ylcarbamate. MS ESI (+) m/z 345.2 (M+1) detected.

Example 23

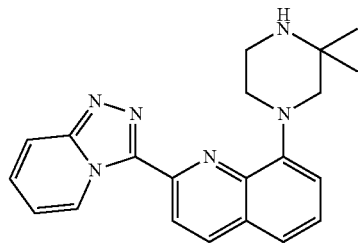 [SMILES: CC1(C)CN(c2cccc3ccc(-c4nnc5ccccn45)nc23)CCN1]

2-([1,2,4]triazolo[4,3-a]pyridin-3-yl)-8-(3,3-dimethylpiperazin-1-yl)quinoline

Prepared as described in Example 21 using tert-butyl 2,2-dimethylpiperazine-1-carboxylate in place of (R)-tert-butyl piperidin-3-ylcarbamate. MS ESI (+) m/z 359.2 (M+1) detected.

Example 24

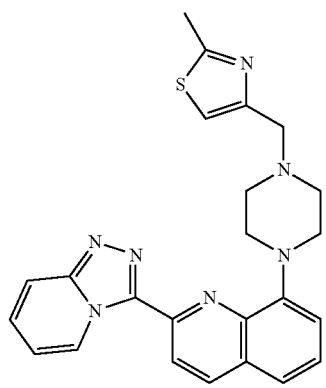 [SMILES: Cc1nc(CN2CCN(c3cccc4ccc(-c5nnc6ccccn56)nc34)CC2)cs1]

4-((4-(2-([1,2,4]triazolo[4,3-a]pyridin-3-yl)quinolin-8-yl)piperazin-1-yl)methyl)-2-methylthiazole Prepared as described in Example 1 using 2-methyl-4-(piperazin-1-ylmethyl)thiazole in place of tert-butyl 4-aminopiperidine-1-carboxylate in step H. MS ESI (+) m/z 442.3 (M+1) detected.

Example 25

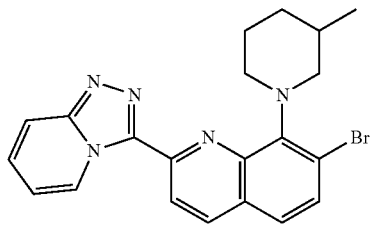 [SMILES: CC1CCCN(c2c(Br)ccc3ccc(-c4nnc5ccccn45)nc23)C1]

2-([1,2,4]triazolo[4,3-a]pyridin-3-yl)-7-bromo-8-(3-methylpiperidin-1-yl)quinoline Step A: Preparation of
7-bromo-2-methylquinolin-8-ol To a 250 mL flask was added toluene (150 mL) and t-BuNH$_2$ (7.26 mL, 69.1 mmol). The solution was cooled to −25° C. and bromine (1.95 mL, 38.0 mmol) was added. The solution was cooled to −78° C. and 2-methylquinolin-8-ol (5.5 g, 34.6 mmol) was added as a CH$_2$Cl$_2$ solution (15 mL). The reaction mixture was then gradually warmed to ambient temperature over 6 hours. The mixture was washed with water (50 mL) and then treated with 3.0 M aqueous NaOH (250 mL). This provided copious amounts of precipitate, which went into solution after about 600 mL water was added. The layers were mixed and separated. The alkaline extract was carefully acidified with concentrated HCl (about 50 mL). The solution was extracted with CH$_2$Cl$_2$ (4×200 mL), and the combined extracts were washed with brine and dried over Na$_2$SO$_4$, filtered and concentrated. The original water wash was found to contain a significant amount of product, so 10 mL 1M HCl was added and the acidic solution was extracted with CH$_2$Cl$_2$ (2×75 mL) and these layers were also washed with brine, dried over Na$_2$SO$_4$, filtered and concentrated. The organic phases were combined to provide 5.0 g (60%) of the desired product as a red/brown solid.

Step B: Preparation of 7-bromo-8-(tert-butyldimethylsilyloxy)-2-methylquinoline

To the product from Step A (3.0 g, 12.6 mmol) was added imidazole (1.89 g, 27.7 mmol) and CH$_2$Cl$_2$ (40 mL). The solution was cooled to 0° C. and then tert-butylchlorodimethylsilane (2.09 g, 13.9 mmol) was added in one portion. The reaction was gradually warmed to ambient temperature over 1 hour and then stirred overnight. The mixture was diluted with a saturated aqueous NH$_4$Cl solution (25 mL) and CH$_2$Cl$_2$ (40 mL). The layers were mixed and separated and the organic layer was washed with brine and dried over Na$_2$SO$_4$, filtered and concentrated. The crude product was purified by column chromatography (2 to 20% CH$_2$Cl$_2$/hexanes) to provide 3.36 g (76%) of the desired product as a white solid.

Step C: Preparation of 7-bromo-8-(tert-butyldimethylsilyloxy)quinoline-2-carbaldehyde A slurry of SeO$_2$ (0.869 g, 7.83 mmol) and 1,4-dioxane (20 mL) was warmed to 80° C. and then the product from Step B (2.3 g, 6.53 mmol) was added as a 1,4-dioxane solution (20 mL). The mixture was stirred at 80° C. for 32 hours. The mixture was cooled to ambient temperature and filtered through GF/F filter paper and the residual solid was washed with CH$_2$Cl$_2$. The filtrate was concentrated and purified by passing through a silica gel plug, eluting with 50% CH$_2$Cl$_2$/hexane to provide 2.14 g (89%) of the product as a yellow/orange solid.

Step D: Preparation of 7-bromo-8-(tert-butyldimethylsilyloxy)-2-((2-(pyridin-2-yl)hydrazono)methyl)quinoline To the product from Step C (2.95 g, 8.05 mmol) was added EtOH (30 mL, anhydrous). To this solution was added 2-hydrazinylpyridine (0.967 g, 8.86 mmol). The mixture was stirred at ambient temperature for 24 hours. The resulting precipitate was isolated by vacuum filtration and washed with cold EtOH and then dried in vacuo to afford 2.98 g (73%) of the desired product.

Step E: Preparation of 2-([1,2,4]triazolo[4,3-a]pyridin-3-yl)-7-bromo-8-(tert-butyldimethylsilyloxy)quinoline To the product from Step D (2.95 g, 6.45 mmol) was added CH$_2$Cl$_2$ (60 mL). Iodobenzene diacetate (2.28 g, 7.09 mmol) was added and the mixture stirred at ambient temperature overnight. The mixture was concentrated and the product purified directly by column chromatography (1 to 8% MeOH/CH$_2$Cl$_2$) to afford 2.87 g (88%) of the product.

Step F

Preparation of 2-([1,2,4]triazolo[4,3-a]pyridin-3-yl)-7-bromoquinolin-8-ol: To the product from Step E (2.8 g, 6.15 mmol) was added THF (60 mL). The solution was cooled to 0° C. then TBAF.3H$_2$O (2.33 g, 7.38 mmol) was added and the mixture was stirred for 1 hour. The mixture was then diluted with EtOAc (100 mL) and then washed with saturated aqueous NaHCO$_3$ (75 mL). The layers were separated and the aqueous phase washed with EtOAc (100 mL). The combined organic phases were washed with brine and dried over Na$_2$SO$_4$, filtered and concentrated. The crude mixture was triturated with MeOH and the mixture was filtered and the solid was washed with Et$_2$O (0.730 g; 35%).

Step G: Preparation of
2-([1,2,4]triazolo[4,3-a]pyridin-3-yl)-7-bromo quinolin-8-yl trifluoromethanesulfonate The product from Step F (0.730 g, 2.14 mmol) was suspended in THF (6 mL) and DMF (2 mL). NEt$_3$ (0.746 mL, 5.35 mmol) was added followed by N-Phenyltriflimide (0.917 g, 2.57 mmol). The mixture was stirred at ambient temperature overnight. There was still starting material present, so additional N-Phenyltriflimide (0.300 g) was added and the reaction stirred for an additional 1.0 hours. The mixture was diluted with water (25 mL), stirred for 30 min and then filtered. The solids were washed with water, Et$_2$O (10 mL) and then hexanes. The solid was dried in vacuo until constant weight 0.890 g (88%) and was used directly in the next step.

Step H: Preparation of 2-([1,2,4]triazolo[4,3-a]pyridin-3-yl)-7-bromo-8-(3-methylpiperidin-1-yl)quinoline The product from Step G (0.025 g, 0.0528 mmol) and 3-methylpiperidine (0.0186 mL, 0.158 mmol) were added to a small microwave reaction vial followed by NMP (0.250 mL). The vessel was placed inside the center of the microwave oven and then it was exposed to microwave irradiation (250 W) for 20 minutes at a temperature of 195° C. After the irradiation, the reaction mixture was cooled to ambient temperature, poured into 10 mL of water and extracted with $CH_2Cl_2$ (3×10 mL). The combined organic extracts were washed with saturated brine and dried over anhydrous $Na_2SO_4$. After removal of the solvent, the residue was purified by column chromatography on silica gel to give the product as a dark orange semisolid which was ~80% pure. This material was purified via Preparative TLC using 50% Acetone/hexane as eluent to provide 0.005 g (22%) of the product as an orange film. MS ESI (+) m/z 422.3 (M) detected.

Example 26

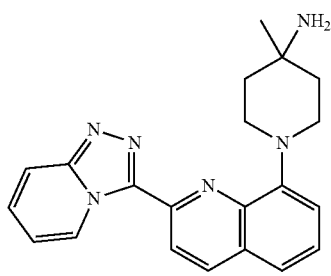 [SMILES: CC1(N)CCN(c2cccc3ccc(-c4nnc5ccccn45)nc23)CC1]

1-(2-([1,2,4]triazolo[4,3-a]pyridin-3-yl)quinolin-8-yl)-4-methylpiperidin-4-amine Step A: Preparation of benzyl 1-(2-([1,2,4]triazolo[4,3-a]pyridin-3-yl)quinolin-8-yl)-4-methylpiperidin-4-ylcarbamate Prepared as described in Example 1 using benzyl 4-methylpiperidin-4-ylcarbamate in place of tert-butyl 4-aminopiperidine-1-carboxylate in step H.

Step B: Preparation of 1-(2-([1,2,4]triazolo[4,3-a]pyridin-3-yl)quinolin-8-yl)-4-methylpiperidin-4-amine To the product from Step A (0.115 g, 0.233 mmol) was added HCl (1.17 mL, 7.00 mmol, 6.0N aqueous). The mixture was stirred at 90° C. for 45 minutes. The mixture was then cooled to ambient temperature and diluted with water (10 mL) and with $CH_2Cl_2$ (10 mL). The layers were mixed and separated and the aqueous phase was washed once more with $CH_2Cl_2$ (10 mL) and was then treated with saturated aqueous $Na_2CO_3$ until pH=10. The aqueous phase was then extracted with $CH_2Cl_2$ (3×10 mL). The combined organic phases were washed with water followed by brine and then dried over $Na_2SO_4$, filtered and concentrated to provide 0.058 g (66%) of the product >96% pure by HPLC. MS ESI (+) m/z 359.1 (M+1) detected.

Example 27

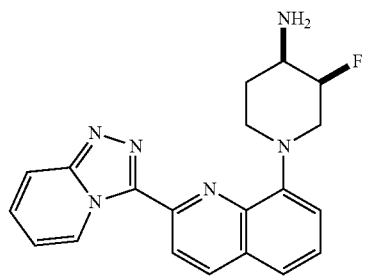 [SMILES: N[C@@H]1CCN(c2cccc3ccc(-c4nnc5ccccn45)nc23)C[C@@H]1F]

(cis)-1-(2-([1,2,4]triazolo[4,3-a]pyridin-3-yl)quinolin-8-yl)-3-fluoropiperidin-4-amine Step A: Preparation of tert-butyl 4-(trimethylsilyloxy)-5,6-dihydropyridine-1(2H)-carboxylate To a 1.0 L flask was added tert-butyl 4-oxopiperidine-1-carboxylate (150.0 g, 752.8 mmol), which was dissolved in DMF (400 mL). To this solution was added TMS-Cl (114.7 mL, 903.4 mmol), followed by $NEt_3$ (251.8 mL, 1807 mmol). The resulting heterogeneous mixture was warmed to 70° C. and stirred overnight under a $N_2$ atmosphere. The mixture was cooled to ambient temperature, diluted with hexanes (250 mL) and filtered. The solids were washed with hexanes (4×250 mL). The combined organic phases were washed with a saturated aqueous $NaHCO_3$ (3×250 mL) and brine (3×250 mL), dried over $Na_2SO_4$, and concentrated. The crude product was carried on directly to the next step.

Step B: Preparation of tert-butyl 3-fluoro-4,4-dihydroxypiperidine-1-carboxylate To the product from Step A (204 g, 750 mmol) was added $CH_3CN$ (1500 mL). To this solution was added Selectfluor (292 g, 825 mmol) portionwise (25 grams every 5 minutes) while cooling the reaction mixture in a water bath. The reaction was stirred for 18 hours at ambient temperature. The mixture was concentrated to dryness and the residue dissolved in EtOAc (750 mL) and brine (500 mL). The organic layer was washed with brine (250 mL) and dried over $Na_2SO_4$, filtered and concentrated to dryness. The crude product was dissolved in minimal EtOAc (150 mL) with heating until the solution was homogeneous and the solution was allowed to cool to ambient temperature. Hexane (100 mL) was added until the solution had become cloudy white. The mixture was allowed to sit undisturbed for about 12 hours and the resulting solid isolated by filtration. This provided 99 g (56%) of the product as a white solid.

Step C: Preparation of tert-butyl 4-(benzylamino)-3-fluoropiperidine-1-carboxylate To a slurry of $NaBH_4$ (7.567 g, 200.0 mmol) in DCE (200 mL) was added 2-Ethylhexanoic acid (95.50 mL, 600.0 mmol) slowly over 30 minutes via addition funnel. The mixture was stirred at ambient temperature for 4 hours with venting to release H₂. In a separate 1 L flask was added the product from Step B (23.53 g, 100 mmol), benzylamine (16.37 mL, 150.0 mmol) and DCE (400 mL). The hydride solution was then added via addition funnel to the mixture over 1 hours while cooling the reaction in a water bath. The reaction was stirred at ambient temperature for 2 days, then diluted with water (100 mL) and concentrated in vacuo to remove solvent. The residue was partitioned between EtOAc (300 mL) and a saturated aqueous Na₂CO₃ solution (2×75 mL). The mixture was shaken, the layers separated and the organic phase washed again with a saturated aqueous Na₂CO₃ solution (100 mL) and finally with brine (50 mL). The aqueous phases were extracted with CHCl₃ (3×75 mL), and the organic phases were dried over Na₂CO₃, filtered and concentrated. The crude product was purified by column chromatography (EtOAc/Hexane) providing 19.55 g of the pure cis product and 5.0 g of a cis/trans mixture (80%).

Step D: Preparation of cis-tent-butyl 4-amino-3-fluoropiperidine-1-carboxylate

To a 250 mL glass Parr vessel was added the product from Step C (14.8 g, 48.0 mmol) and EtOH (100 mL). Pearlman's Catalyst (4.72 g, 3.36 mmol) was added and the mixture was shaken in a Parr reactor under 40-45 psi H₂ for 15 hours. The reaction was filtered through celite and the celite was washed with EtOAc. The filtrate was concentrated and the residue was dissolved in CH₂Cl₂ and filtered through celite, and the celite was washed with CH₂Cl₂ and EtOAc. The filtrate was concentrated to afford 10.2 g (92%) of the desired product as a thick oil that slowly solidified to a white solid.

Step E: Preparation of cis-tent-butyl 4-(benzyloxycarbonylamino)-3-fluoropiperidine-1-carboxylate To a solution of the product from Step D (10 g, 45.8 mmol) in THF (90 mL) and water (20 mL) was added K₂CO₃ (8.23 g, 59.6 mmol). Once the solid was dissolved benzyl chloroformate (7.19 mL, 50.4 mmol) was added. The reaction was stirred vigorously at ambient temperature for 5.0 hours. Once the reaction was complete by TLC the reaction was diluted with EtOAc (100 mL) and water (20 mL). The layers were separated and the organic layer was washed with brine, then dried over Na₂SO₄, filtered and concentrated in vacuo. The product was purified by column chromatography (EtOAc/hexane) to afford 12.9 g (80%) of a sticky, white foam.

Step F: Preparation of cis-benzyl-3-fluoropiperidin-4-ylcarbamate (cis)-tert-Butyl 4-(benzyloxycarbonylamino)-3-fluoropiperidine-1-carboxylate (7.5 g, 21.3 mmol) was weighed into a 500 mL 1 neck round bottom and dissolved in 200 mL of DCM, followed by addition of TFA (16.4 mL, 213 mmol) and stirring at ambient temperature for 1 hour, at which time all bubbling had ceased and the reaction appeared complete by TLC. The crude reaction was concentrated in vacuo, followed by aqueous work-up with 2 N NaOH and DCM. The combined organics were dried over Na₂SO₄, filtered and concentrated in vacuo to afford benzyl (cis)-3-fluoropiperidin-4-ylcarbamate (4.25 g, 16.8 mmol, 79.2% yield) as a white solid.

Step G: Preparation of cis-benzyl 1-(2-([1,2,4]triazolo[4,3-a]pyridin-3-yl)quinolin-8-yl)-3-fluoropiperidin-4-ylcarbamate Prepared as described in Example 1 using cis-benzyl-3-fluoropiperidin-4-ylcarbamate in place of tent-butyl 4-aminopiperidine-1-carboxylate in step H.

Step H: Preparation of 1-(2-([1,2,4]triazolo[4,3-a] pyridin-3-yl)quinolin-8-yl)-3-fluoropiperidin-4-amine To the product from Step G (0.185 g, 0.373 mmol) was added HCl (1.86 mL, 11.2 mmol, 6.0M aqueous) and the solution was warmed to 90° C. and stirred for 0.5 hours. The mixture was cooled to ambient temperature and diluted with water (10 mL) and with CH₂Cl₂ (10 mL). The layers were mixed and separated and the aqueous phase was treated with saturated aqueous Na₂CO₃ until pH=10. The aqueous phase was extracted with CH₂Cl₂ (4×10 mL). The combined organic phase was washed with water and brine, dried over Na₂SO₄, filtered and concentrated. The crude residue was purified by column chromatography (1 to 10% MeOH w/6% NH₄OH/CH₂Cl₂) to afford 0.094 g (69%) of the desired product as a pale yellow/orange solid. MS ESI (+) m/z 363.2 (M+1) detected.

What is claimed is:
1. A compound of general Formula I:

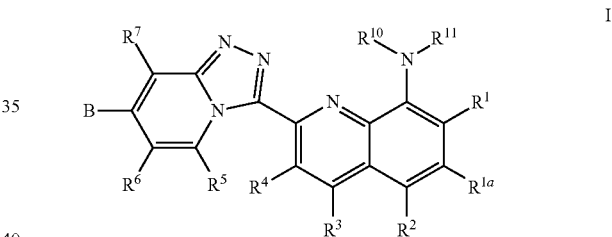

or a pharmaceutically acceptable salt thereof, wherein:
$R^{10}$ and $R^{11}$ together with the N to which they are attached form a 4-8 membered heterocyclic ring optionally having an additional ring heteroatom selected from N and O, wherein the heterocyclic ring is optionally substituted with one or more $R^9$ groups;
each $R^9$ is independently selected from halogen, (1-6C) alkyl, $NR^fR^g$, -(1-6C alkyl)$NR^hR^i$, $OR^j$, (1-6C alkyl)$OR^k$, $C(O)NR^mR^n$, $C(O)O$(1-6C alkyl), and -(1-6C alkyl)$NR^hC(O)O$(1-6C alkyl);
B is H, $OR^a$, (1-6C alkyl)$NR^bR^c$, (1-6C alkyl)OH, $NR^bR^c$, or $CH(OH)CH_2OH$;
$R^1$ is H, F, Cl, Br, methyl, ethyl, cyclopropyl or CN;
$R^{1a}$, $R^2$, $R^3$ and $R^4$ are independently H, F, Cl, Br, methyl, ethyl, cyclopropyl or CN;
$R^5$ and $R^7$ are independently H, F, Me or CN;
$R^6$ is H, F, Me, Br, CN, cyclopropyl or phenyl;
$R^a$ is H, (1-6C alkyl), -(1-6C alkyl)-O-(1-6C alkyl) or -(1-6C alkyl)-O-(3-6C cycloalkyl);
each $R^b$, $R^c$, $R^d$, $R^e$, $R^f$, $R^g$, $R^h$, $R^i$, $R^j$, $R^k$, and $R^m$ is independently selected from H and (1-6C alkyl); and
$R^n$ is H, (1-6C alkyl) or O-(1-6C alkyl).
2. A compound of claim 1, wherein $NR^{10}R^{11}$ forms a heterocyclic ring selected from piperidinyl, piperazinyl, and morpholinyl, each of which is unsubstituted or substituted with one or more $R^9$ groups.

3. A compound of claim 1, wherein each $R^9$ is independently selected from Me, $NH_2$, $CH_2NH_2$, OH, $CH_2OH$, C(O)OMe, C(O)$NH_2$ and $CH_2NHCO_2$t-Bu.

4. A compound of claim 1, wherein B is H.

5. A compound of claim 1, wherein B is $OR^a$.

6. A compound of claim 5, wherein B is selected from OMe and —$OCH_2CH_2OMe$.

7. A compound of claim 1, wherein B is (1-6C alkyl)$NR^bR^c$.

8. A compound of claim 7, wherein B is $CH_2NHEt$ or $CH_2H_2$.

9. A compound of claim 1, wherein B is (1-6C alkyl)OH.

10. A compound of claim 9, wherein B is $CH_2OH$.

11. A compound of claim 1, wherein B is $CH(OH)CH_2OH$.

12. A compound of claim 1, wherein $R^{1a}$ is H, F or Cl.

13. A compound of claim 1, wherein $R^2$ is H or F.

14. A compound of claim 1, wherein $R^3$ and $R^4$ are H.

15. A compound of claim 1, wherein $R^5$, $R^6$ and $R^7$ are H.

16. A pharmaceutical composition, which comprises a compound of Formula I of claim 1, or a pharmaceutically acceptable salt thereof, and a pharmaceutically acceptable diluent or carrier.

17. A process for the preparation a compound of claim 1, which comprises:

(a) coupling a corresponding compound having the formula II

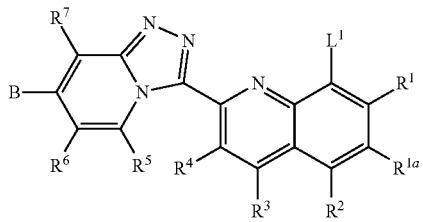

wherein $L^1$ represents a leaving atom or group, with a compound having the formula $HNR^{10}R^{11}$ wherein $NR^{10}R^{11}$ represents a 4-8 membered heterocyclic ring optionally having an additional heteroatom selected from N and O and optionally substituted with one or more $R^9$ groups, using a palladium catalyst and a ligand in the presence of a base; or (b) reacting a compound of Formula III

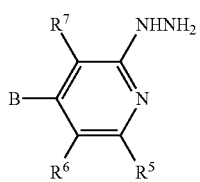

with a compound having the Formula IV

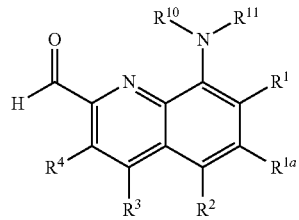

in the presence of an organo hypervalent iodine reagent; or (c) for a compound of Formula I where B is $Or^a$, reacting a corresponding compound having the Formula V

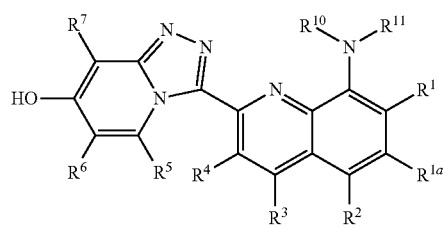

with a compound of the formula $R^a$-$L^2$, wherein $L^2$ represents a leaving atom or group, in the presence of a base;

(d) for a compound of Formula I wherein B is ($CH_2$)$NR^bR^c$, reacting a corresponding compound having the Formula VI

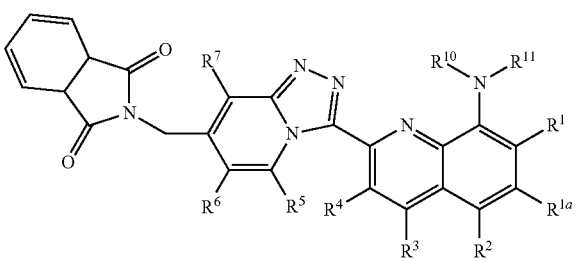

with hydrazine; and removing any protecting group or groups and, if desired, forming a salt.

* * * * *

UNITED STATES PATENT AND TRADEMARK OFFICE
CERTIFICATE OF CORRECTION

PATENT NO. : 8,557,809 B2  
APPLICATION NO. : 13/059881  
DATED : October 15, 2013  
INVENTOR(S) : Allen et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 277 days.

Signed and Sealed this  
Tenth Day of March, 2015

Michelle K. Lee  
*Deputy Director of the United States Patent and Trademark Office*